(12) United States Patent
Barnhart et al.

(10) Patent No.: US 10,449,146 B2
(45) Date of Patent: Oct. 22, 2019

(54) METHODS OF TREATING PARKINSON'S DISEASE BY ADMINISTRATION OF APOMORPHINE TO AN ORAL MUCOSA

(71) Applicant: Sunovion Pharmaceuticals Inc., Marlborough, MA (US)

(72) Inventors: Scott David Barnhart, York, PA (US); Michael Clinton Koons, York, PA (US); Madhu Sudan Hariharan, Greensboro, NC (US); Jordan Dubow, Glencoe, IL (US); Thierry Bilbault, Toronto (CA); Anthony John Giovinazzo, Caledon (CA)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 15/789,528

(22) Filed: Oct. 20, 2017

(65) Prior Publication Data
US 2018/0133146 A1    May 17, 2018

Related U.S. Application Data

(63) Continuation of application No. PCT/US2016/028265, filed on Apr. 19, 2016.

(60) Provisional application No. 62/150,624, filed on Apr. 21, 2015.

(51) Int. Cl.
| | | |
|---|---|---|
| *A61K 9/00* | (2006.01) | |
| *A61K 47/02* | (2006.01) | |
| *A61K 31/473* | (2006.01) | |
| *A61K 45/06* | (2006.01) | |
| *A61K 47/14* | (2017.01) | |
| *A61K 47/26* | (2006.01) | |
| *A61K 47/36* | (2006.01) | |
| *A61K 9/70* | (2006.01) | |
| *A61P 25/16* | (2006.01) | |
| *A61K 47/10* | (2017.01) | |
| *A61K 47/18* | (2017.01) | |
| *A61K 47/38* | (2006.01) | |

(52) U.S. Cl.
CPC ............ *A61K 9/006* (2013.01); *A61K 9/7007* (2013.01); *A61K 31/473* (2013.01); *A61K 45/06* (2013.01); *A61K 47/02* (2013.01); *A61K 47/10* (2013.01); *A61K 47/14* (2013.01); *A61K 47/183* (2013.01); *A61K 47/26* (2013.01); *A61K 47/36* (2013.01); *A61K 47/38* (2013.01); *A61P 25/16* (2018.01)

(58) Field of Classification Search
CPC ...... A61K 31/473; A61K 45/06; A61K 47/02; A61K 47/10; A61K 47/14; A61K 47/183; A61K 47/26; A61K 47/36; A61K 47/38; A61K 9/006; A61K 9/7007; A61P 25/16
See application file for complete search history.

(56) References Cited

U.S. PATENT DOCUMENTS

| | | |
|---|---|---|
| 3,972,995 A | 8/1976 | Tsuk et al. |
| 4,614,545 A | 9/1986 | Hess |
| 5,047,244 A | 9/1991 | Sanvordeker et al. |
| 5,441,747 A | 8/1995 | de Haan et al. |
| 5,523,090 A | 6/1996 | Znaiden et al. |
| 5,560,932 A | 10/1996 | Bagchi et al. |
| 5,624,677 A | 4/1997 | El-Rashidy et al. |
| 5,629,003 A | 5/1997 | Horstmann et al. |
| 5,700,478 A | 12/1997 | Biegajski et al. |
| 5,888,534 A | 3/1999 | El-Rashidy et al. |
| 5,945,117 A | 8/1999 | El-Rashidy et al. |
| 5,994,363 A | 11/1999 | El-Rashidy et al. |
| 6,087,362 A | 7/2000 | El-Rashidy |
| 6,121,276 A | 9/2000 | El-Rashidy et al. |
| 6,159,498 A | 12/2000 | Tapolsky et al. |
| 6,177,096 B1 | 1/2001 | Zerbe et al. |
| 6,193,992 B1 | 2/2001 | El-Rashidy et al. |
| 6,200,983 B1 | 3/2001 | El-Rashidy et al. |
| 6,264,981 B1 | 7/2001 | Zhang et al. |
| 6,284,264 B1 | 9/2001 | Zerbe et al. |
| 6,306,437 B1 | 10/2001 | El-Rashidy et al. |
| 6,316,027 B1 | 11/2001 | Johnson et al. |
| 6,375,963 B1 | 4/2002 | Repka et al. |
| 6,486,207 B2 | 11/2002 | Yeager et al. |
| 6,488,953 B2 | 12/2002 | Halliday et al. |
| 6,552,024 B1 | 4/2003 | Chen et al. |
| 6,566,368 B2 | 5/2003 | El-Rashidy et al. |
| 6,667,056 B2 | 12/2003 | Chiesi et al. |
| 6,756,407 B2 | 6/2004 | Heaton et al. |

(Continued)

FOREIGN PATENT DOCUMENTS

| | | |
|---|---|---|
| AU | 746373 B2 | 4/2002 |
| CA | 2274893 A1 | 6/1998 |

(Continued)

OTHER PUBLICATIONS

Bala et al., "Orally dissolving strips: A new approach to oral drug delivery system", 2013, Int. J. Pharma. Investig., 3(2), pp. 67-76. (Year: 2013).*

(Continued)

*Primary Examiner* — My-Chau T. Tran
(74) *Attorney, Agent, or Firm* — Clark & Elbing LLP

(57) ABSTRACT

Methods and pharmaceutical unit dosage forms for treating Parkinson's disease in a subject (e.g., an "off" episode in a subject having Parkinson's disease) are described. The pharmaceutical unit dosage forms are films having a first portion including particles containing an acid addition salt of apomorphine and a second portion containing a pH neutralizing agent. The pharmaceutical unit dosage forms can be flexible and have toughness greater than 100 gxmm. The methods can involve administering to a subject having Parkinson's disease a therapeutic dose sufficient to produce an apomorphine plasma concentrate of at least 2.64 ng/mL within 45 minutes after the administration. The subject may be identified as having low uptake, medium uptake, or high uptake of apomorphine administered via oral mucosa.

13 Claims, 10 Drawing Sheets

(56) References Cited

U.S. PATENT DOCUMENTS

| | | |
|---|---|---|
| 6,974,590 B2 | 12/2005 | Pather et al. |
| 7,037,526 B1 | 5/2006 | Krumme et al. |
| 7,087,240 B1 | 8/2006 | Fotinos |
| 7,332,230 B1 | 2/2008 | Krumme |
| 7,357,891 B2 | 4/2008 | Yang et al. |
| 7,374,782 B2 | 5/2008 | Brown |
| 7,425,292 B2 | 9/2008 | Yang et al. |
| 7,579,019 B2 | 8/2009 | Tapolsky et al. |
| 7,666,337 B2 | 2/2010 | Yang et al. |
| 7,824,588 B2 | 11/2010 | Yang et al. |
| 7,897,080 B2 | 3/2011 | Yang et al. |
| 7,910,031 B2 | 3/2011 | Yang et al. |
| 7,910,641 B2 | 3/2011 | Myers |
| 8,017,150 B2 | 9/2011 | Yang et al. |
| 8,414,922 B2 | 4/2013 | Bryson et al. |
| 8,603,514 B2 | 12/2013 | Yang et al. |
| 8,652,378 B1 | 2/2014 | Yang et al. |
| 8,658,201 B2 | 2/2014 | Singh et al. |
| 8,663,687 B2 | 3/2014 | Myers et al. |
| 8,685,437 B2 | 4/2014 | Yang et al. |
| 8,765,167 B2 | 7/2014 | Myers et al. |
| 8,846,074 B2 | 9/2014 | Bryson et al. |
| 9,044,475 B2 | 6/2015 | Giovinazzo et al. |
| 9,283,219 B2 | 3/2016 | Bryson et al. |
| 9,326,981 B2 | 5/2016 | Giovinazzo et al. |
| 9,427,412 B2 | 8/2016 | Bryson et al. |
| 9,669,018 B2 | 6/2017 | Giovinazzo et al. |
| 9,669,019 B2 | 6/2017 | Giovinazzo et al. |
| 9,669,020 B2 | 6/2017 | Giovinazzo et al. |
| 9,669,021 B2 | 6/2017 | Giovinazzo et al. |
| 2001/0006677 A1 | 7/2001 | McGinity et al. |
| 2002/0115683 A1 | 8/2002 | Ruff et al. |
| 2003/0022912 A1 | 1/2003 | Martino et al. |
| 2003/0073715 A1 | 4/2003 | El-Rashidy et al. |
| 2003/0096012 A1 | 5/2003 | Besse et al. |
| 2003/0107149 A1 | 6/2003 | Yang et al. |
| 2004/0028613 A1 | 2/2004 | Quay |
| 2004/0063742 A1 | 4/2004 | Peters et al. |
| 2004/0204440 A1 | 10/2004 | Staniforth et al. |
| 2005/0031677 A1 | 2/2005 | Pather et al. |
| 2005/0037055 A1 | 2/2005 | Yang et al. |
| 2005/0226823 A1 | 10/2005 | Krumme et al. |
| 2006/0141032 A1 | 6/2006 | Larsen |
| 2006/0198873 A1 | 9/2006 | Chan et al. |
| 2006/0210610 A1 | 9/2006 | Davidson et al. |
| 2007/0149479 A1 | 6/2007 | Fischer et al. |
| 2007/0149731 A1 | 6/2007 | Myers |
| 2008/0008753 A1 | 1/2008 | Singh |
| 2008/0057087 A1 | 3/2008 | Krumme |
| 2008/0119504 A1 | 5/2008 | Wikstrom et al. |
| 2008/0124381 A1 | 5/2008 | Barnhart et al. |
| 2009/0023766 A1 | 1/2009 | Clarke |
| 2010/0035886 A1 | 2/2010 | Cincotta et al. |
| 2011/0033542 A1 | 2/2011 | Myers et al. |
| 2011/0111011 A1 | 5/2011 | Giovinazzo et al. |
| 2013/0337148 A1 | 12/2013 | Yang et al. |
| 2016/0095851 A1 | 4/2016 | Giovinazzo et al. |
| 2016/0338972 A1 | 11/2016 | Bryson et al. |

FOREIGN PATENT DOCUMENTS

| | | |
|---|---|---|
| CN | 1271276 A | 10/2000 |
| DE | 19652268 A1 | 6/1998 |
| JP | 2001-506612 A | 5/2001 |
| JP | 2002-531393 A | 9/2002 |
| JP | 2004-520389 A | 7/2004 |
| JP | 2004-534839 A | 11/2004 |
| JP | 2004-535361 A | 11/2004 |
| JP | 2005-263704 A | 9/2005 |
| JP | 2006-508060 A | 3/2006 |
| JP | 2007-517053 A | 6/2007 |
| JP | 2008-540392 A | 11/2008 |
| JP | 2009-521532 A | 6/2009 |
| JP | 5760295 B2 | 8/2015 |
| KR | 2000-0057627 A | 9/2000 |
| KR | 2008-0016608 A | 2/2008 |
| KR | 10-2014-0043051 A | 4/2014 |
| RU | 2189226 C2 | 9/2002 |
| RU | 2283650 C1 | 9/2006 |
| WO | WO-93/25168 A1 | 12/1993 |
| WO | WO-96/41619 A1 | 12/1996 |
| WO | WO-97/06786 A1 | 2/1997 |
| WO | WO-98/26763 A1 | 6/1998 |
| WO | WO-98/48781 A1 | 11/1998 |
| WO | WO-00/32171 A2 | 6/2000 |
| WO | WO-00/042992 A2 | 7/2000 |
| WO | WO-02/056808 A1 | 7/2002 |
| WO | WO-02/062315 A1 | 8/2002 |
| WO | WO-02/100377 A1 | 12/2002 |
| WO | WO-03/000018 A2 | 1/2003 |
| WO | WO-03/005944 A1 | 1/2003 |
| WO | WO-2004/026309 A1 | 4/2004 |
| WO | WO-2004/045537 A2 | 6/2004 |
| WO | WO-2004/066986 A1 | 8/2004 |
| WO | WO-2005/018323 A1 | 3/2005 |
| WO | WO-2005/065318 A2 | 7/2005 |
| WO | WO-2006/031209 A1 | 3/2006 |
| WO | WO-2006/039264 A1 | 4/2006 |
| WO | WO-2006/120412 A1 | 11/2006 |
| WO | WO-2007/030754 A2 | 3/2007 |
| WO | WO-2007/067494 A1 | 6/2007 |
| WO | WO-2007/075422 A2 | 7/2007 |
| WO | WO-2008/011194 A2 | 1/2008 |
| WO | WO-2008/039737 A2 | 4/2008 |
| WO | WO-2008/040534 A2 | 4/2008 |
| WO | WO-2008/100375 A2 | 8/2008 |
| WO | WO-2009/052421 A1 | 4/2009 |
| WO | WO-2010/144817 A1 | 12/2010 |
| WO | WO-2011/143424 A1 | 11/2011 |
| WO | WO-2012/053006 A2 | 4/2012 |
| WO | WO-2012/083269 A1 | 6/2012 |
| WO | WO-2014/049140 A1 | 4/2014 |

OTHER PUBLICATIONS

"Cynapsus Receives FDA Fast Track Designation for APL-130277 for the Treatment of OFF Episodes in Patients with Parkinson's Disease," Globe Newswire, available <https://globenewswire.com/news-release/2016/08/29/867552/0/en/Cynapsus-Receives-FDA-Fast-Track-Designation-for-APL-130277-for-the-Treatment-of-OFF-Episodes-in-Patients-with-Parkinson-s-Disease.html>, dated Aug. 29, 2016 (3 pages).

"Fast Track," available <http://www.fda.gov/ForPatients/Approvals/Fast/ucm405399.htm>, accessed Oct. 28, 2016 (2 pages).

"R-(−)-Apomorphine hydrochloride hemihydrate, calcined," <http://www.sigmaaldrich.com/content/dam/sigma-aldrich/docs/Sigma/Product_Information_Sheet/a4393pis.pdf>, accessed on Oct. 26, 2015 (1 page).

"Sunovion Pharmaceuticals to Acquire Cynapsus Therapeutics," dated Aug. 31, 2016 (6 pages).

Ahlskog et al., "Frequency of levodopa-related dyskinesias and motor fluctuations as estimated from the cumulative literature," Mov Disord. 16(3):448-58 (2001).

Ang et al., "Stability of apomorphine in solutions containing selected antioxidant agents," Drug Des Devel Ther. 10:3253-65 (2016).

Annexes I-III, Product Information for Ixense, European Medicines Agency, London, United Kingdom, 2004 (27 pages).

APO-go Ampoules 10mg/ml Package Leaflet, Feb. 2013 (2 pages).

APOKYN Prescribing information, Britannia Pharmaceuticals Limited, available <http://www.apokyn.com/assets/APOKYN_PI.pdf>, 2004 (16 pages).

Aquino et al., "Clinical spectrum of levodopa-induced complications," Mov Disord. 30(1):80-9 (2015).

Arny, The Pyridine and Quinoline Derivatives. *Principles of Pharmacy*. W. B. Saunders, p. 823 (1917).

Bhidayasiri et al., "Effective delivery of apomorphine in the management of Parkinson disease: practical considerations for clinicians and Parkinson nurses," Clin Neuropharmacol. 38(3):89-103 (2015).

(56) References Cited

OTHER PUBLICATIONS

Burkman, "Some kinetic and thermodynamic characteristics of apomorphine degradation," J Pharm Sci. 54:325-6 (1965).
Chapter 55: Pharmaceutical Necessities and Chapter 57: Drug Absorption, Action, and Dispositon. Remington: The Science and Practice of Pharmacy. Gennaro, 1015, 1098-1126 (2000) (33 pages).
Chapter 9: Basic Biopharmaceutics of Buccal and Sublingual Absorption and Chapter 10: Chemical Enchancers in Buccal and Subligual Absorptions. *Enhancement in Drug Delivery*. Touitou and Barry, 175-213 (2007) (21 pages).
Chapuis et al., "Impact of the motor complications of Parkinson's disease on the quality of life," Mov Disord. 20(2):224-30 (2005).
Cohn et al., "The measurement of the acidity of bread," J Biol Chem. 36:581-6 (1918).
Cotzias et al., "Similarities between neurologic effects of L-dopa and of apomorphine," N Engl J Med. 282(1):31-3 (1970).
Decker et al., "A stable parenteral solution of apomorphine," Clin Toxicol. 18(7):763-72 (1981).
Deffond et al., "Apomorphine in treatment of Parkinson's disease: comparison between subcutaneous and sublingual routes," J Neurol Neurosurg Psychiatry. 56(1):101-3 (1993).
del Consuelo, "Ex vivo evaluation of bioadhesive films for buccal delivery of fentanyl," J Control Release. 122(2):135-40 (2007).
Design and Evaluation of Oral Administration Formulations, 1995, p. 199 (2 pages).
Durif et al., "Apomorphine and diphasic dyskinesia," Clin Neuropharmacol. 17(1):99-102 (1994).
Gandhi et al., "Oral cavity as a site for bioadhesive drug delivery," Adv Drug Deliv Rev. 13(1-2):43-74 (1994).
Goswami et al., "Sublingual drug delivery," Crit Rev Ther Drug Carrier Syst. 25(5):449-84 (2008).
Harris et al., "Drug delivery via the mucous membranes of the oral cavity," J Pharm Sci. 81(1):1-10 (1992).
HBM Pharma/Biotech M&A Report 2016, Jan. 2016 (16 pages).
Holloway et al., "Pramipexole vs levodopa as initial treatment for Parkinson disease: a 4-year randomized controlled trial," Arch Neurol. 61(7):1044-53 (2004) (11 pages).
Hornykiewicz, "Basic research on dopamine in Parkinson's disease and the discovery of the nigrostriatal dopamine pathway: the view of an eyewitness," Neurodegener Dis. 5(3-4):114-7 (2008).
Hughes et al., "Sublingual apomorphine in the treatment of Parkinson's disease complicated by motor fluctuations," Clin Neuropharmacol. 14(6):556-61 (1991).
International Preliminary Report on Patentability for International Application No. PCT/US16/28265, dated Oct. 24, 2017 (7 pages).
International Search Report for International Application No. PCT/US16/28265, dated Jul. 29, 2016 (3 pages).
Kaul et al., "Auto-oxidation of apomorphine," J Pharm Sci. 50(3):266-7 (1961).
Koller et al., "Other formulations and future considerations for apomorphine for subcutaneous injection therapy," Neurology. 62(6 Suppl 4):S22-S26 (2004).
Lees et al., "Sublingual apomorphine and Parkinson's disease," J Neurol Neurosurg Psychiatry. 52(12):1440 (1989) (2 pages).
López et al., "Motor complications in Parkinson's disease: ten year follow-up study," Mov Disord. 25(16):2735-9 (2010).
Michael J Fox Foundation, MJFF Off Time Survey, "Executive Summary: Survey of Parkinson's Patients and Their Off Time Experience" (2 pages).
Michael J Fox Foundation, MJFF Survey—Off Time Survey Results, "Impact of Parkinson's Disease Off Episodes," Aug. 11, 2014 (13 pages).
Montastruc et al., "Sublingual apomorphine in Parkinson's disease: a clinical and pharmacokinetic study," Clin Neuropharmacol. 14(5):432-437 (1991).
Ng Ying Kin et al., "Stability of apomorphine hydrochloride in aqueous sodium bisulphite solutions," Prog Neuropsychopharmacol Biol Psychiatry. 25(7):1461-8 (2001).
Oertel et al., "Pergolide versus levodopa monotherapy in early Parkinson's disease patients: The PELMOPET study," Mov Disord 21(3):343-53 (2006).
Olanow et al., "Factors predictive of the development of Levodopa-induced dyskinesia and wearing-off in Parkinson's disease," Mov Disord. 28(8):1064-71 (2013).
Ondo et al., "Apomorphine injections: predictors of initial common adverse events and long term tolerability," Parkinsonism Relat Disord. 18(5):619-22 (2012).
Ondo et al., "Efficacy and tolerability of a novel sublingual apomorphine preparation in patients with fluctuating Parkinson's disease," Clin Neuropharmacol. 22(1):1-4 (1999).
Ondo et al., "Novel sublingual apomorphine treatment for patients with fluctuating Parkinson's disease," Movement Disorders. 14(4):664-8 (1999).
Rascol et al., "A five-year study of the incidence of dyskinesia in patients with early Parkinson's disease who were treated with ropinirole or levodopa," N Engl J Med. 342(20):1484-91 (2000).
Reproductive Health Drugs Advisory Committee, Urology Subcommittee, FDA Briefing Package, Apr. 10, 2000 (18 pages).
Ribaric, "The pharmacological properties and therapeutic use of apomorphine," Molecules. 17(5):5289-309 (2012).
Rizos et al., "Characterizing motor and non-motor aspects of early-morning off periods in Parkinson's disease: an international multicenter study," Parkinsonism Relat Disord. 20(11):1231-5 (2014).
Sam et al., "Stability of apomorphine in plasma and its determination by high-performance liquid chromatography with electrochemical detection," J Chromatogr B Biomed Appl. 658(2):311-17 (1994).
Sanchez et al., "Interplay of chromatographic parameters and analyte physical properties on retention and selectivity in hydrophilic interaction liquid chromatography," Phenomenex, Inc., (2007) (18 pages).
Semalty et al., "Formulation and characterization of mucoadhesive buccal films of glipizide," Indian J Pharm Sci. 70(1):43-8 (2008).
Skoog et al., Theory of Neutralization Titrations. Fundamentals of Analytical Chemistry. 7:202 (1996).
Tan et al., "Functional COMT variant predicts response to high dose pyridoxine in Parkinson's disease," Am J Med Genet B Neuropsychiatr Genet. 137B(1):1-4 (2005).
Tanner et al., "Epidemiology of Parkinson's disease," Neurol Clin. 14(2):317-35 (1996).
Tsai et al., "Oral apomorphine delivery from solid lipid nanoparticles with different monostearate emulsifiers: pharmacokinetic and behavioral evaluations," J Pharm Sci. 100(2):547-557 (2011).
van Laar et al., "A new sublingual formulation of apomorphine in the treatment of patients with Parkinson's disease," Mov Disord. 11(6):633-8 (1996).
Weast (ed.), *CRC Handbook of Chemistry and Physics 52nd Edition*. The Chemical Rubber Company (1971) (p. D-119).
Wilcox et al., "Stability of apomorphine in solutions containing ascorbic acid and bisulfite and effects of antioxidants on apomorphine-induced cage climbing and hypothermia in mice," J Pharm Sci. 69(8):974-6 (1980).
Written Opinion for International Application No. PCT/US16/28265, dated Jul. 29, 2016 (6 pages).
Wüllner et al., "Requirements for Parkinson's disease pharmacotherapy from the patients' perspective: a questionnaire-based survey," Curr Med Res Opin. 28(7):1239-46 (2012).
Statement of Grounds for Appeal for European Patent No. 2442650, mailed Jun. 25, 2018 (116 pages).
Interlocutory Decision in Opposition Proceedings (Art. 101(3)(a) and 106(2) EPC) for European Patent No. 2442650, dated Feb. 15, 2018 (25 pages).
Extended European Search Report for European Application No. 16783684.0, dated Oct. 25, 2018 (8 pages).

\* cited by examiner

METHODS OF TREATING PARKINSON'S DISEASE BY ADMINISTRATION OF APOMORPHINE TO AN ORAL MUCOSA

FIELD OF THE INVENTION

In general, this invention relates to methods of, and pharmaceutical compositions for, treating Parkinson's disease. The methods may involve administering to an oral mucosa of a subject a therapeutic dose of apomorphine.

BACKGROUND

Parkinson's disease (PD) is a progressive degenerative disease of the central nervous system. The risk of developing Parkinson's disease increases with age, and afflicted individuals are usually adults over 40. Parkinson's disease occurs in all parts of the world, and affects more than 1.5 million individuals in the United States alone.

While the primary cause of Parkinson's disease is not known, it is characterized by degeneration of dopaminergic neurons of the substantia nigra. The substantia nigra is a portion of the lower brain, or brain stem that helps control voluntary movements. The shortage of dopamine in the brain caused by the loss of these neurons is believed to cause the observable disease symptoms.

The symptoms of PD vary from patient to patient. The most common symptom is a paucity of movement and rigidity, characterized by an increased stiffness of voluntary skeletal muscles. Additional symptoms include resting tremor, bradykinesia (slowness of movement), poor balance, and walking problems. Common secondary symptoms include depression, sleep disturbance, dizziness, stooped posture, dementia, problems with speech, breathing, and swallowing. The symptoms become progressively worse with time and ultimately result in death.

A variety of therapeutic treatments for PD are available. Perhaps the best known is levodopa, a dopamine precursor. While levodopa administration can result in a dramatic improvement in symptoms, patients can experience serious side-effects, including nausea and vomiting. Moreover, many patients develop involuntary choreiform movements which are the result of excessive activation of dopamine receptors. These movements usually affect the face and limbs and can become very severe. Such movements disappear if the dose of dopamine precursor (e.g., levodopa) or dopamine agonist is reduced, but this typically causes rigidity to return. Moreover, the margin between the beneficial and the unwanted effects (i.e., the therapeutic window) appears to become progressively narrower as the period of treatment lengthens.

A further complication of long-term treatment with certain dopamine receptor modulators (e.g., dopamine precursors or agonists) is the development of rapid fluctuations in clinical state where the patient switches suddenly between mobility and immobility for periods ranging from a few minutes to a few hours. The fluctuations are of several general types. "Wearing-off" phenomena are deteriorations in the relief afforded by a dose of levodopa before the next dose takes effect (Van Laar T., CNS Drugs, 17:475, 2003). Because they are related to a patient's dose schedule, such periods are often relatively predictable (Dewey RB Jr., Neurology, 62(suppl 4):S3-S7, 2004). In contrast, "on-off" phenomena are sudden transitions from an "on" period of levodopa benefit to an "off" period of akinesia, rigidity, and tremor that occur in minutes or even seconds, (Swope DM., Neurology, 62(suppl 4):S27-S31 (2004)) with no discernible relation to a patient's dose schedule. Two other phenomena are the delayed "on" effect, in which levodopa's effects are substantially delayed, and dose failure (also known as the no-"on" or skipped-dose effect), in which no effects occur at all. These various "off" states can produce such an abrupt loss of mobility that the patient may suddenly stop while walking or be unable to rise from a chair in which he had sat down normally a few moments earlier.

Subcutaneous injections of apomorphine have proved to be effective in the treatment of "on-off" fluctuations in Parkinson's disease within 7 to 23 minutes, and last for 45 to 90 minutes. Trials have shown consistent reversal of "off" period akinesia. Advantages over other dopamine agonists include a quick onset of action and lower incidence of psychological complications. For a "rescue therapy" in patients with "on-off" fluctuations, apomorphine also has the advantage over other dopamine agonists, as it has a relatively short half-life.

Numerous formulations and routes of administration for apomorphine have been studied and apomorphine therapy has been found to be hampered by various complications. For example, oral administration of apomorphine tablets has required high doses to achieve the necessary therapeutic effect because apomorphine administered by this route undergoes extensive metabolism in the small intestine and/or, upon absorption, in the liver; sublingual administration of apomorphine tablets caused severe stomatitis on prolonged use with buccal mucosal ulceration in half the patients treated (see Deffond et al., J. Neurol. Neurosurg. Psychiatry 56:101, 1993); and intranasal administration produced transient nasal blockage, burning sensation and swollen nose and lips (see Koller et al., Neurology 62:S22, 2004). While subcutaneous injections of apomorphine have proven effective, an injection by needle is difficult for Parkinson's patients because of impaired motor function. Furthermore, a common side effect of subcutaneous injection is the development of nodules, which often become infected, necessitating antiobiotic treatment or surgical debridement (see Prietz et al., J. Neurol. Neurosurg. Psychiatry 65:709, 1998).

There is a need for new apomorphine regimens which are safe, effective, and easy for a Parkinson's patient to use. In particular, there is a need for the regimens that are efficacious in a wide patient population while reducing the possibility for adverse events.

SUMMARY OF THE INVENTION

The invention features methods of, and pharmaceutical unit dosage forms for, treating Parkinson's disease (e.g., for treating an "off" episode in a subject having Parkinson's disease).

In a first aspect, the invention features a method of treating Parkinson's disease in a subject (e.g., an "off" episode in a subject having Parkinson's disease), the method involves:

(a) providing a film having a first portion including apomorphine particles containing an acid addition salt of apomorphine and a second portion containing a pH neutralizing agent; and (b) administering the film to an oral mucosa of the subject (e.g., sublingually), where the film contains an acid addition salt of apomorphine in an amount sufficient to produce, on average, following administration to subjects: (i) an apomorphine plasma concentration of at least 2.64 ng/mL within 30 minutes, and (ii) the apomorphine Cmax in said subject is less than 10 ng/mL (e.g., less than 9 ng/mL, less than 8 ng/mL, less than 7 ng/mL, less than 6 ng/mL, less than 5 ng/mL, or less than 4.7 ng/mL).

In some embodiments of the first aspect, the film contains 10±2.5 mg, 12.5±2.5 mg, or 15±2.5 mg (e.g., 12.5±2.5 mg) of an acid addition salt of apomorphine (e.g., when administered to the subjects have high sublingual uptake in response to apomorphine administered to oral mucosa (e.g., sublingually)). In certain embodiments of the first aspect, the film contains 15.0±2.5 mg, 20.0±2.5 mg, or 25.0±2.5 mg (e.g., 17.5±2.5 mg) of an acid addition salt of apomorphine (e.g., when administered to the subjects have medium sublingual uptake in response to apomorphine administered to oral mucosa (e.g., sublingually)). In particular embodiments, the film contains 30.0±5.0 mg, 35.0±5.0 mg, or 40.0±5.0 mg (e.g., 25.0±5.0 mg) of an acid addition salt of apomorphine (e.g., when administered to the subjects have low sublingual uptake in response to apomorphine administered to oral mucosa (e.g., sublingually)). In further embodiments, step (a) involves determining responsiveness of the subject to apomorphine by titration (e.g., uptitration).

In a second aspect, the invention features a method of treating Parkinson's disease in a subject (e.g., an "off" episode in a subject having Parkinson's disease). The method involves:
  (a) providing a subject identified by titration as having low uptake, medium uptake, or high uptake in response to sublingually administered apomorphine; and
  (b) (1) if the subject is a subject identified as having low uptake in response to sublingually administered apomorphine, sublingually administering a therapeutic dose containing 10±2.5 mg, 12.5±2.5 mg, or 15±2.5 mg of an acid addition salt of apomorphine to the subject;
  (2) if the subject is a subject identified as having medium uptake in response to sublingually administered apomorphine, sublingually administering a therapeutic dose containing 15.0±2.5 mg, 20.0±2.5 mg, or 25.0±2.5 mg of an acid addition salt of apomorphine to the subject; or
  (3) if the subject is a subject identified as having high uptake in response to sublingually administered apomorphine, sublingually administering a therapeutic dose containing 30.0±5.0 mg, 35.0±5.0 mg, or 40.0±5.0 mg of an acid addition salt of apomorphine to the subject;

where the therapeutic dose is administered in the form of a film having a first portion including apomorphine particles containing an acid addition salt of apomorphine and a second portion containing a pH neutralizing agent. The therapeutic dose administered to a subject identified as having low uptake in response to sublingually administered apomorphine is greater than the therapeutic dose administered to a subject identified as having medium uptake in response to sublingually administered apomorphine. Also, the therapeutic dose administered to a subject identified as having medium uptake in response to sublingually administered apomorphine is greater than the therapeutic dose administered to a subject identified as having high uptake in response to sublingually administered apomorphine.

In some embodiments of the second aspect, in step (b), the combinations (1), (2), and (3) take on the following values:
  i) (1) 10±2.5 mg, (2) 15.0±2.5 mg, and (3) 30.0±5.0 mg;
  ii) (1) 10±2.5 mg, (2) 15.0±2.5 mg, and (3) 35.0±5.0 mg;
  iii) (1) 10±2.5 mg, (2) 15.0±2.5 mg, and (3) 40.0±5.0 mg;
  iv) (1) 10±2.5 mg, (2) 20.0±2.5 mg, and (3) 30.0±5.0 mg;
  v) (1) 10±2.5 mg, (2) 20.0±2.5 mg, and (3) 35.0±5.0 mg;
  vi) (1) 10±2.5 mg, (2) 20.0±2.5 mg, and (3) 40.0±5.0 mg;
  vii) (1) 10±2.5 mg, (2) 25.0±2.5 mg, and (3) 30.0±5.0 mg;
  vii) (1) 10±2.5 mg, (2) 25.0±2.5 mg, and (3) 35.0±5.0 mg;
  ix) (1) 10±2.5 mg, (2) 25.0±2.5 mg, and (3) 40.0±5.0 mg;
  x) (1) 12±2.5 mg, (2) 15.0±2.5 mg, and (3) 30.0±5.0 mg;
  xi) (1) 12±2.5 mg, (2) 15.0±2.5 mg, and (3) 35.0±5.0 mg;
  xii) (1) 12±2.5 mg, (2) 15.0±2.5 mg, and (3) 40.0±5.0 mg;
  xiii) (1) 12±2.5 mg, (2) 20.0±2.5 mg, and (3) 30.0±5.0 mg;
  xiv) (1) 12±2.5 mg, (2) 20.0±2.5 mg, and (3) 35.0±5.0 mg;
  xv) (1) 12±2.5 mg, (2) 20.0±2.5 mg, and (3) 40.0±5.0 mg;
  xvi) (1) 12±2.5 mg, (2) 25.0±2.5 mg, and (3) 30.0±5.0 mg;
  xvii) (1) 12±2.5 mg, (2) 25.0±2.5 mg, and (3) 35.0±5.0 mg;
  xviii) (1) 15±2.5 mg, (2) 25.0±2.5 mg, and (3) 40.0±5.0 mg;
  xix) (1) 15±2.5 mg, (2) 15.0±2.5 mg, and (3) 30.0±5.0 mg;
  xx) (1) 15±2.5 mg, (2) 15.0±2.5 mg, and (3) 35.0±5.0 mg;
  xxi) (1) 15±2.5 mg, (2) 15.0±2.5 mg, and (3) 40.0±5.0 mg;
  xxii) (1) 15±2.5 mg, (2) 20.0±2.5 mg, and (3) 30.0±5.0 mg;
  xxiii) (1) 15±2.5 mg, (2) 20.0±2.5 mg, and (3) 35.0±5.0 mg;
  xxiv) (1) 15±2.5 mg, (2) 20.0±2.5 mg, and (3) 40.0±5.0 mg;
  xxv) (1) 15±2.5 mg, (2) 25.0±2.5 mg, and (3) 30.0±5.0 mg;
  xxvi) (1) 15±2.5 mg, (2) 25.0±2.5 mg, and (3) 35.0±5.0 mg; or
  xxvii) (1) 15±2.5 mg, (2) 25.0±2.5 mg, and (3) 40.0±5.0 mg;

provided that the value in (3)>the value in (2)>the value in (1).

In particular embodiments of the first or second aspect, prior to administering an acid addition salt of apomorphine, the subject is administered an effective amount of an antiemetic. In certain embodiments of the first or second aspect, an effective amount of the antiemetic is administered to the subject for at least 2 days prior to administering the apomorphine.

In a third aspect, the invention features a pharmaceutical unit dosage form that is a film containing a first portion including particles of an acid addition salt of apomorphine and a second portion containing a pH neutralizing agent and a permeation enhancer.

In some embodiments of any aspect, the film has a toughness greater than or equal to 100 g×mm (e.g., greater than or equal to 150 g×mm). In certain embodiments of any aspect, the film has a toughness in the range from 100 g×mm to 1000 g×mm (e.g., from 100 g×mm to 800 g×mm or from 150 g×mm to 800 g×mm).

In particular embodiments of any aspect, the second portion contains a permeation enhancer. In certain embodiments of any aspect, the first portion contains a permeation enhancer. In other embodiments of any aspect, the first portion is free of a permeation enhancer. In further embodiments of any aspect, the film comprises less than 10% (w/w) (e.g., from 0.001% (w/w) to 10% (w/w), from 0.1% (w/w) to 10% (w/w), or from 0.1% (w/w) to 5% (w/w)) of a permeation enhancer. In yet other embodiments of any aspect, each permeation enhancer is independently menthol, an ionic surfactant, a nonionic surfactant, a polysorbate, a tocopherol derivative, a poloxamer, a monoglyceride, a diglyceride, a fatty acid, or a fatty alcohol, or a combination thereof. In particular embodiments of any aspect, the permeation enhancer is a combination of menthol and glycerol monostearate.

In some embodiments of any aspect, the film contains 20% (w/w) or more of a pharmaceutically acceptable high molecular weight polymer having a weight average molecular weight of 60 kDa or greater. In certain embodiments of any aspect, the film contains from 20% (w/w) to 40% (w/w) of the pharmaceutically acceptable high molecular weight polymer. In particular embodiments of any aspect, the pharmaceutically acceptable high molecular weight polymer has a weight average molecular weight from 60 kDa to 1,000 kDa (e.g., from 60 kDa to 500 kDa). In other embodiments of any aspect, the pharmaceutically acceptable high molecular weight polymer is carboxymethylcellulose, hydroxypropyl cellulose, hydroxypropyl methyl cellulose, hydroxyethyl cellulose, or methyl cellulose, or a combination thereof.

In certain embodiments of any aspect, the film contains 5% (w/w) or less (e.g., from 0.01% (w/w) to 5% (w/w), from 0.1% (w/w) to 4% (w/w), or from 1% (w/w) to 3% (w/w)) of a pharmaceutically acceptable low molecular weight polymer having a weight average molecular weight of less than 60 kDa (e.g., from 5 kDa to 50 kDa). In particular embodiment of any aspect, the pharmaceutically acceptable low molecular weight polymer is carboxymethylcellulose, hydroxypropyl cellulose, hydroxypropyl methyl cellulose, hydroxyethyl cellulose, or methyl cellulose, or a combination thereof. In some embodiments of any aspect, the pharmaceutically acceptable low molecular weight polymer is hydroxypropyl cellulose. In other embodiments of any aspect, the second portion is free of a pharmaceutically acceptable low molecular weight polymer In particular embodiments of any aspect, the pharmaceutical unit dosage form of the invention contains from 2 mg to 60 mg (e.g., from 8 mg to 45 mg) of the acid addition salt of apomorphine (e.g., apomorphine hydrochloride). In other embodiments of any aspect, the pharmaceutical unit dosage form of the invention contains, e.g., 10.0±2.0 mg, 12.5±2.5 mg, 15.0±2.5 mg, 17.5±2.5 mg, 20.0±5.0 mg, 25.0±5.0 mg, 30.0±10.0 mg, 30.0±5.0 mg, 35.0±10.0 mg, 35.0±5.0 mg, or 40.0±5.0 mg of an acid addition salt of apomorphine (e.g., apomorphine hydrochloride). In certain embodiments of any aspect, the pharmaceutical unit dosage form of the invention contains, e.g., 10.0±2.0 mg, 12.5±2.5 mg, 15.0±2.5 mg, 20.0±5.0 mg, 25.0±5.0 mg, 30.0±5.0 mg, 35.0±5.0 mg, or 40.0±5.0 mg of an acid addition salt of apomorphine (e.g., apomorphine hydrochloride). In any aspect, the acid addition salt of apomorphine may be apomorphine hydrochloride.

In some embodiments of any aspect, the pH neutralizing agent is an organic base having a pKa of 5±2 (e.g., pyridoxine, meglumine, lysine, Eudragit E, diethanolamine, glycine, citrate, acetate, histidine, N-methyl glucamine, or tris(hydroxymethyl)aminomethane). In particular embodiments of any aspect, the pH neutralizing agent is pyridoxine.

In particular embodiments of any aspect, the film disintegrates in aqueous media (e.g., water) in 2 minutes or less (e.g., in 110 second or less or in 100 seconds or less). In certain embodiments of any aspect, the film disintegrates in aqueous media (e.g., water) in 30 seconds or more (e.g., in 40 second or more or in 50 seconds or more). In some embodiments of any aspect, the film disintegrates in aqueous media (e.g., water) in a period of time that is in the range from 30 seconds to 2 minutes (e.g., from 40 seconds to 1 minute, from 1 minute to 2 minutes, or from 50 seconds to 100 seconds).

In certain embodiments of any aspect, the film is a multilayer film (e.g., a bilayer film).

In particular embodiments of any aspect, the pharmaceutical unit dosage form, when administered in an effective amount, maintains an apomorphine plasma concentration of at least 2.64 ng/mL (e.g., at least 2.7 ng/mL, at least 2.8 ng/mL, or at least 2.9 ng/mL) for a period of at least 60 minutes (e.g., at least 70 minutes, at least 80 minutes, or at least 90 minutes).

In some embodiments of any aspect, when administered to the subject in an effective amount, the film produces apomorphine Tmax from 10 minutes to 60 minutes (e.g., from 20 minutes to 60 minutes, from 30 minutes to 60 minutes, from 10 minutes to 20 minutes, from 10 minutes to 30 minutes, from 10 minutes to 40 minutes, from 10 minutes to 50 minutes, from 20 minutes to 30 minutes, from 20 minutes to 40 minutes, from 20 minutes to 50 minutes, from 30 minutes to 40 minutes, or from 30 minutes to 50 minutes) following the administration to an oral mucosa of the subject (e.g., sublingually). In certain embodiment of any aspect, when administered to the subject in an effective amount, the film produces apomorphine Cmax from 2.64 ng/mL to 10 ng/mL (e.g., from 2.64 ng/mL to 9 ng/mL, 8 ng/mL, 7 ng/mL, 6 ng/mL, 5 ng/mL, or from 2.64 ng/mL to 4.7 ng/mL) in the subject. In particular embodiments of any aspect, a pharmaceutical unit dosage form can contain an effective amount of an acid addition salt of apomorphine and produce Cmax of from 2.64 ng/mL to 7.1 ng/mL and Tmax of from 30 minutes to 50 minutes after administration of the pharmaceutical unit dosage form to the subject. In other embodiments of any aspect, a pharmaceutical unit dosage form can contain an effective amount of an acid addition salt of apomorphine and produce Cmax of from 2.64 ng/mL to 5.0 ng/mL and Tmax of from 20 minutes to 60 minutes after administration of the pharmaceutical unit dosage form to the subject. In yet other embodiments of any aspect, a pharmaceutical unit dosage form can contain an effective amount of an acid addition salt of apomorphine and produce Cmax of from 2.64 ng/mL to 4.7 ng/mL and Tmax of from 30 minutes to 60 minutes after administration of the pharmaceutical unit dosage form to the subject. In certain other embodiments of any aspect, a pharmaceutical unit dosage form can contain an effective amount of an acid addition salt of apomorphine and produce Cmax of from 2.64 ng/mL to 5.0 ng/mL (e.g., from 2.64 ng/mL to 4.7 ng/mL) and Tmax of from 10 minutes to 30 minutes after administration of the pharmaceutical unit dosage form to the subject. In particular embodiments of any aspect, a pharmaceutical unit dosage form produces fewer adverse events in a subject, when administered in an effective amount to the subject. In some embodiments of any aspect, the reduced adverse event is somnolescence, nausea, yawning, headache, or hyperhidrosis.

DEFINITIONS

The term "about," as used herein, refers to a number that is ±10% of the recited value.

The term "Cmax," as used herein, refers to an average observed maximum plasma concentration produced in a group of subjects (e.g., 10 or more) receiving an apomorphine film in an amount sufficient to produce an "on" state, where the amount of the film administered for each individual subject is the lowest effective amount administered during up-titration of the individual subject (i.e., the Cmax accounting for variations in bioavailability) for a given route of administration (e.g., to oral mucosa, such as sublingual).

The term "effective amount," as used herein in reference to apomorphine, refers to a quantity of apomorphine administered to a subject at once so as to produce at least one of the following effects: (1) a plasma concentration of at least 2.64 ng/mL of apomorphine in the subject within 45 minutes (e.g., within 30 minutes) of the administration; and (2) the subject in an "on" state within 45 minutes (e.g., within 30 minutes) of administering the administration.

The term "fewer adverse events," as used herein, refers to an average observed number and severity of adverse events produced in a group of subjects (e.g., 10 or more) receiving an apomorphine film in an amount sufficient to produce an "on" state following administration of the film of the invention in comparison to the average number and severity of adverse events produced in a group of subjects (e.g., 10 or more) receiving a unit dosage form producing a higher Cmax. The Cmax produced by the film of the invention can be from 2.64 ng/mL to 10 ng/mL (e.g., from 2.64 ng/mL to 9 ng/mL, 8 ng/mL, 7 ng/mL, 6 ng/mL, 5 ng/mL, or from 2.64 ng/mL to 4.7 ng/mL), optionally, with a Tmax of from 25 minutes to 70 minutes (e.g., from 30 minutes to 70 minutes, from 35 minutes to 60 minutes, from 30 minutes to 50 minutes, from 30 minutes to 40 minutes, or from 30 minutes to 70 minutes). Some pharmaceutical unit dosage forms of the invention thus can produce an "on" state and fewer adverse in a subject by providing Cmax of from 2.64 ng/mL to 7.1 ng/mL and Tmax of from 30 minutes to 50 minutes after administration of the pharmaceutical unit dosage form to the subject. Certain pharmaceutical unit dosage forms of the invention thus can produce an "on" state and fewer adverse in a subject by providing Cmax of from 2.64 ng/mL to 5.0 ng/mL and Tmax of from 25 minutes to 60 minutes after administration of the pharmaceutical unit dosage form to the subject. Particular pharmaceutical unit dosage forms of the invention thus can produce an "on" state and fewer adverse in a subject by providing Cmax of from 2.64 ng/mL to 4.7 ng/mL and Tmax of from 30 minutes to 60 minutes after administration of the pharmaceutical unit dosage form to the subject. Certain other pharmaceutical unit dosage forms of the invention thus can produce an "on" state and fewer adverse in a subject by providing Cmax of from 2.64 ng/mL to 5.0 ng/mL (e.g., from 2.64 ng/mL to 4.7 ng/mL) and Tmax of from 25 minutes to 40 minutes after administration of the pharmaceutical unit dosage form to the subject. The adverse events may be, e.g., somnolescence, nausea, yawning, headache, or hyperhidrosis.

The term "pH neutralizing agent," as used herein, refers to any basic component present in the unit dosage forms of the invention. The pH neutralizing agents which can be used in the unit dosage forms of the invention include organic bases (e.g., pyridoxine, meglumine, lysine, Eudragit E, diethanolamine, glycine, citrate, acetate, histidine, N-methyl glucamine, or tris(hydroxymethyl)aminomethane), inorganic bases (e.g., oxides, hydroxides, carbonates, or phosphates), and mixtures thereof. The pH neutralizing agent is typically present in an amount sufficient to produce a solution having a pH of between 2.5 and 8.0, preferably between 4.5 and 6.5, when the unit dosage form is placed in 1 mL of unbuffered water at pH 7.

The term "subject," as used herein, refers to a human having Parkinson's disease. The subject may be diagnosed as having Parkinson's disease through the use of techniques known in the art, e.g., unified Parkinson's disease rating scale (UPDRS) or Hoehn and Yahr scale.

The term "Tmax," as used herein, refers to an average observed time to the maximum plasma concentration produced in a group of subjects (e.g., 10 or more) receiving an apomorphine film in an amount sufficient to produce an "on" state, where the amount of the film administered for each individual subject is the lowest effective amount administered during up-titration of the individual subject (i.e., the Tmax accounting for variations in bioavailability) for a given route of administration (e.g., to oral mucosa, such as sublingual).

DETAILED DESCRIPTION

Figure 1:
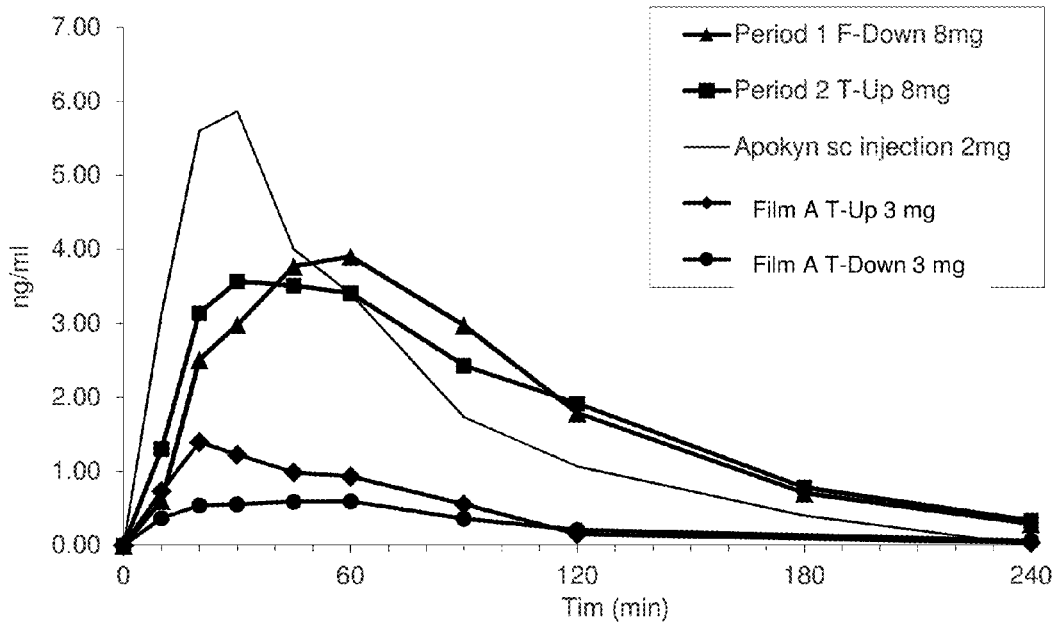
FIG. 1 is a chart showing pharmacokinetic curves for Film A, Film B (labeled as Period 1 and Period 2), and 2 mg subcutaneous Apokyn®.

The present invention relates to methods and compositions for treating Parkinson's disease in a subject (e.g., hypomobility or an "off" episode in a subject having Parkinson's disease). The methods are based on the discovery that subjects receiving apomorphine treatment via oral mucosa (e.g., sublingually) do not appear to exhibit a narrowing of the apomorphine therapeutic window with disease progression in contrast to those undergoing therapy with certain other dopamine receptor modulators. Further, subject-to-subject variations in apomorphine dosing efficacy appear to relate to the individual capability of each subject to uptake apomorphine or an acid addition salt thereof via oral mucosa. Accordingly, identification of the subject's capability to uptake apomorphine or an acid addition salt thereof via oral mucosa can allow for (1) reduced dosing of subjects showing high uptake of apomorphine or an acid addition salt thereof via oral mucosa (e.g., sublingually), and (2) increase of apomorphine or an acid addition salt thereof dosage for subjects showing low uptake via oral mucosa (e.g., sublingually). Advantageously, occurrence of adverse effects can be reduced by administering lower dosages of apomorphine or an acid addition salt thereof to the oral mucosa of a subject showing high apomorphine uptake via oral mucosa; and, without risking a high rate of adverse effects related to high plasma concentration of apomorphine, a higher dosage of apomorphine or an acid addition salt thereof can be administered to the oral mucosa of a subject showing low apomorphine uptake via oral mucosa.

The invention also features a pharmaceutical unit dosage form that is a film containing: (1) a first portion including particles containing an acid addition salt of apomorphine and (2) a second portion containing a pH neutralizing agent. The pharmaceutical unit dosage form may exhibit toughness that is desirable for a product intended for self-administration by the subject having Parkinson's disease and thus exhibiting diminished motor skills. In particular, fragility of the pharmaceutical unit dosage form lacking requisite mechanical properties may hinder its self-administration by the subject having Parkinson's disease, which may lead to incorrect (e.g., insufficient) apomorphine dosing. Thus, the pharmaceutical unit dosage form of the invention may exhibit toughness greater than or equal to 100 g×mm (e.g., greater than or equal to 150 g×mm). Moreover, toughness of the pharmaceutical unit dosage forms of the invention renders them easier to manufacture at a relatively faster rate than more fragile formulations. Toughness provides a measure of tensile strength and is a product of burst force and the distension of the film during the burst force test, which measures the force required to puncture the film with a standard probe. The test useful in determining the toughness of the pharmaceutical unit dosage form of the invention is *Film and Laminate Puncturing Test*, ASTM F1306.

The methods and compositions of the invention are further characterized by a finding that apomorphine or an acid addition salt thereof, when administered to oral mucosa, exhibits minimum effective concentration of about 2.64 ng/mL, whereas minimum effective concentration of apomorphine in subjects having Parkinson's disease was determined to be 4.7 ng/mL for intravenous infusion (van Laar et al., *Clin. Neuropharmacol.*, 21:152-158, 1998).

The dosage forms and methods of the invention can reduce the adverse events associated with apomorphine therapy.

Methods of Treatment

The invention features a method of treating Parkinson's disease in a subject (e.g., treating hypomobility or an "off" episode" in a subject having Parkinson's disease). The method involves administering to oral mucosa of a subject (e.g., sublingually) an oral apomorphine film having a first portion including particles containing apomorphine or an acid addition salt thereof and a second portion containing a pH neutralizing agent. Prior to administering the film, the subject may have been identified as having low uptake; medium uptake; or high uptake of apomorphine via oral mucosa (e.g., sublingual uptake). The film administered in accordance with the methods of the invention can be selected from a plurality of predetermined doses of varying strength having sufficient apomorphine content to produce at least the minimum effective concentration of apomorphine (i.e., at least 2.64 ng/mL). All embodiments of the pharmaceutical unit dosage forms described herein can be used in accordance with the methods of the invention.

Pharmacokinetics/Pharmacodynamics

The minimum effective concentration of apomorphine can be achieved within 30 minutes of administering the oral apomorphine film to the subject in accordance with some methods of the invention. Preferably, an apomorphine $C_{max}$ of less than 30 ng/mL (e.g., less than 20 ng/mL, less than 10 ng/mL, less than 7 ng/mL or less than 5 ng/mL) is produced after administering the film in accordance with the methods of the invention. For example, apomorphine $C_{max}$ may be in the range from 2.64 ng/mL to 30 ng/mL (e.g., from 2.64 ng/mL to 20 ng/mL, from 2.64 ng/mL to 10 ng/mL, or from 2.64 ng/mL to 5 ng/mL). Preferably, $T_{max}$ for apomorphine films administered in accordance with the methods of the invention is in the range of from 10 minutes to 1 hour (e.g., from 20 minutes to 1 hour, or from 20 minutes to 50 minutes).

The subject treated in accordance with the methods of the invention may be identified as having low uptake; medium uptake; or high uptake of apomorphine administered via oral mucosa (e.g., sublingually). The identification of the subject may be performed using methods known in the art, e.g., titration. Preferably, titration is uptitration.

Uptitration may involve administering to oral mucosa of a subject a first predetermined dosage of apomorphine (e.g., 12.5±2.5 mg of an acid addition salt of apomorphine), and determining if an effective amount of apomorphine was administered; if the amount of administered apomorphine was an effective amount, the subject is identified as having a high uptake of apomorphine via oral mucosa (e.g., sublingual uptake). If the amount of apomorphine is determined to be not an effective amount, a second predetermined dosage of apomorphine (e.g., 20.0±5.0 mg of an acid addition salt of apomorphine) is administered to the oral mucosa of the subject, and it is determined if an effective amount of apomorphine was administered with the second predetermined dosage. If the amount of apomorphine administered with the second predetermined is determined to be not an effective amount, a third predetermined dosage of apomorphine (e.g., 30.0±5.0 mg of an acid addition salt of apomorphine) is administered to the oral mucosa of the subject, and it is determined if an effective amount of apomorphine was administered with the third predetermined dosage. One of skill in the art will recognize, that third predetermined dosage contains more acid addition salt of apomorphine than the second predetermined dosage, which contains more acid addition salt of apomorphine than the first predetermined dosage. The determination if an effective amount of apomorphine was administered in any one of the above uptitration steps can be executed in accordance with methods known in the art, e.g., by evaluating UPDRS (e.g., UPDRS Part III) for the subject within a predetermined period (e.g., 30 minutes or 45 minutes) after administering apomorphine or by measuring apomorphine plasma concentration in a blood sample obtained from the subject within a predetermined period (e.g., 30 minutes or 45 minutes) after administering apomorphine.

Pharmaceutical Unit Dosage Forms

Pharmaceutical unit dosage forms of the invention are films containing a first portion and a second portion. The films can be flexible. A pharmaceutical unit dosage form of the invention may contain an acid addition salt of apomorphine and pharmaceutically acceptable excipients, such as a pharmaceutically acceptable polymer, a permeation enhancer, a hydrolyzed starch, an antioxidant, a plasticizing agent, a flavoring agent, and a coloring agent. References to a single pharmaceutically acceptable excipient include mixtures of pharmaceutically acceptable excipients within the scope of the recited type.

The pharmaceutical unit dosage forms of the invention may possess mechanical properties acceptable for ease of handling, e.g., toughness greater than or equal to 100 g×mm (e.g., greater than or equal to 150 g×mm). In particular, toughness of the pharmaceutical unit dosage forms of the invention may be in the range from 100 g×mm to 1000 g×mm (e.g., from 100 g×mm to 800 g×mm or from 150 g×mm to 800 g×mm). The pharmaceutical unit dosage forms can be flexible. Flexibility of pharmaceutical unit dosage forms may be controlled by varying the content of a plasticizing agent (e.g., glycerol) as described below. Toughness of the pharmaceutical unit dosage forms can be enhanced further by using pharmaceutically acceptable polymers of the invention as described below.

The portions in the pharmaceutical unit dosage forms can be domains or layers. In some embodiments, the portions are layers. In certain pharmaceutical unit dosage forms of the invention, the first portion may be free of the pH neutralizing agent to prevent premature neutralization of the acid addition salt of apomorphine, thereby enhancing the film shelf-life by preventing oxidative degradation of neutralized apomorphine.

Pharmaceutically Acceptable Polymers

The pharmaceutically acceptable polymers can be used to control toughness of the pharmaceutical unit dosage form of the invention. In particular, pharmaceutical unit dosage forms of the invention containing at least 20% (w/w) of a pharmaceutically acceptable high molecular weight polymer having a weight average molecular weight ($M_w$) that is greater than or equal to 60 kDa can exhibit a desirable degree of toughness (e.g., at least 100 g×mm or at least 150 g×mm). The pharmaceutical unit dosage form can contain 20% (w/w) or more (e.g., from 20% (w/w) to 50% (w/w), from 20% (w/w) to 40% (w/w), or from 20% (w/w) to 30% (w/w)) of a pharmaceutically acceptable high molecular weight polymer having a weight average molecular weight ($M_w$) that is greater than or equal to 60 kDa (e.g., from 60 kDa to 1,000 kDa).

The first portion may contain a pharmaceutically acceptable high molecular weight polymer having a weight average molecular weight ($M_w$) of 60 kDa or greater (e.g., from 60 kDa to 1,000 kDa). The second portion may contain a pharmaceutically acceptable high molecular weight polymer having a weight average molecular weight ($M_w$) of 60 kDa or greater (e.g., from 60 kDa to 1,000 kDa). In some embodiments, the pharmaceutically acceptable high molecular weight polymer has a weight average molecular weight ($M_w$) from 60 kDa to 500 kDa.

The first portion may contain a pharmaceutically acceptable low molecular weight polymer having a weight average molecular weight ($M_w$) less than 60 kDa (e.g., from 5 kDa to 50 kDa). The second portion may contain a pharmaceutically acceptable low molecular weight polymer having a weight average molecular weight ($M_w$) less than 60 kDa (e.g., from 5 kDa to 50 kDa). In certain unit dosage forms of the invention, the second portion is free of an added polymer having a weight average molecular weight less than 60 kDa (e.g., a pharmaceutically acceptable cellulose derivative having a weight average molecular weight less than 60 kDa). The pharmaceutical unit dosage form of the invention may contain less than 5% (w/w) of a pharmaceutically acceptable low molecular weight polymer (e.g., from 0.01% (w/w) to 5% (w/w), from 0.1% (w/w) to 4% (w/w), or from 1% (w/w) to 3% (w/w)).

Each pharmaceutically acceptable polymer can be independently carboxymethylcellulose, hydroxypropyl cellulose (HPC, such as Nisso HPC SSL, Nippon Soda Co., Ltd., Japan), hydroxypropyl methyl cellulose (also known as hypromellose or HPMC; commercially available under the tradename Methocel™ from Dow Chemical Company, Midland, Mich.), hydroxyethyl cellulose (HEC, commercially available from Hercules Incorporated, Aqualon Division under the tradename NATROSOL™), or methyl cellulose (such as Methocel™, Dow Chemical Company, Midland, Mich.), or a combination thereof.

Plasticizing Agents

The pharmaceutical unit dosage forms of the invention can include a plasticizing agent. Plasticizers will generally modify the feel, softness, flexibility (in an un-wetted state) of the unit dosage forms of the invention. Examples of plasticizers include, without limitation, glycerol, propylene glycol, fatty acid esters, such as glyceryl oleate, polyalcohols, sorbitan esters, citric acid esters, polyethylene glycol (e.g., PEG 400), polyvinyl alcohol, polyvinyl methyl ether, triacetin; mannitol, xylitol, and sorbitol. In some embodiments, the plasticizing agent is glycerol. A pharmaceutical unit dosage form of the invention can contain a plasticizing agent in the amount greater than 0% (w/w) and less than or equal to 8.5% (w/w) (e.g., in the range from 4% (w/w) to 8% (w/w)). In some embodiments, the pharmaceutical unit dosage form contains less than 5% (w/w) of a plasticizing agent (e.g., from 4% (w/w) to 5% (w/w) of a plasticizing agent). By including less than 8.5% (w/w) of a plasticizing agent in the pharmaceutical unit dosage form, the toughness of the pharmaceutical unit dosage forms of the invention is improved. However, some plasticizing agent can be present for flexibility of the pharmaceutical unit dosage form of the invention.

Permeation Enhancers

Pharmaceutical unit dosage forms of the invention can contain a permeation enhancer. For example, in some pharmaceutical unit dosage forms of the invention, the second portion contains a permeation enhancer. In certain pharmaceutical unit dosage forms of the invention, the first portion may be free of a permeation enhancer. The pharmaceutical unit dosage form of the invention can contain less than 10% (w/w) (e.g., from 0.001% (w/w) to 10% (w/w)) of a permeation enhancer.

Permeation enhancers can be used to improve the permeability of the dopamine agonist at the mucosal membrane in the unit dosage forms of the invention. One or more permeation enhancers maybe used to modulate the rate of mucosal absorption of the dopamine agonist. Any effective permeation enhancers may be used including, for example, ionic surfactants, nonionic surfactants, bile salts, such as sodium cholate, sodium glycocholate, sodium glycodeoxycholate, taurodeoxycholate, sodium deoxycholate, sodium lithocholate chenocholate, chenodeoxycholate, ursocholate, ursodeoxy-cholate, hyodeoxycholate, dehydrocholate, glycochenocholate, taurochenocholate, and taurochenodeoxycholate; sodium dodecyl sulfate (SDS), dimethyl sulfoxide (DMSO), N-lauroyl sarcosine, sorbitan monolaurate, stearyl methacrylate, N-dodecylazacycloheptan-2-one, N-dodecyl-2-pyrrolidinone, N-dodecyl-2-piperidinone, 2-(1-nonyl)-1,3-dioxolane, N-(2-methoxymethyl) dodecylamine, N-dodecylethanolamine, N-dodecyl-N-(2-methoxymethyl)acetamide, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 2-dodecyl-2-oxo-1-pyrrolidineacetic acid, 1-azacylioheptan-2-one-dodecylacetic acid, menthol, propylene glycol, glycerol monostearate, sorbitol monolaurate, glycerol dilaurate, tocopherol acetate, phosphatidyl choline, glycerol, polyethyleneglycol, monoglycerides, such as glycerol monostearate, glycerol monoloaurate, glycerol caprylate, diglycerides, triglycerides, and succinylated diglycerides and monoglycerides, such as glycerol succinyl caprylate lecithin, tween surfactants, sorbitan surfactants, sodium lauryl sulfate; salts, acids and other derivatives of saturated and unsaturated fatty acids, fatty alcohols, surfactants, bile salt analogs, derivatives of bile salts, or such synthetic permeation enhancers as described in U.S. Pat. No. 4,746,508, which is incorporated herein by reference.

pH Neutralizing Agents

The pH neutralizing agent can be, for example, a film formed from a basic polymer. Polyamines which can be used in the unit dosage forms of the invention include homo and copolymers of dimethylaminoethyl-acrylate, dimethylaminoethyl-methacrylate, dimethylaminopropyl-acrylate, dimethylaminopropyl-methacrylate, or other similar amino-functionalized acrylate, chitosan or partially hydrolyzed chitin in a substantially basic form, homo and co polymers of polyethyleimine, polylysine, polyvinylimidazole, or polyvinylamine. In certain embodiments the polyamine is Eudragit E100.

Alternatively, the pH neutralizing agent can be a nonpolymeric additive incorporated into a unit dosage form of the invention. The pH neutralizing agent can be an inorganic base (e.g., aluminum hydroxide, aluminosilicates, calcium hydroxide, magnesium hydroxide, potassium hydroxide, sodium hydroxide, calcium carbonate, iron carbonate, magnesium carbonate, zinc carbonate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, or a mixture thereof). The pH neutralizing agent can be an organic base (e.g., acetate salts, citrate salts, stearate salts, laurate salts, proprionate salts, lactate salts, succinate salts, oxalate salts, tartrate salts, glycolate salts, galacturonate salts, glucuronate salts, alginate salts, sorbate salts, caprylate salts, carboxymethyl cellulose, polyacrylate; or amines, such as pyridoxine, meglumine, lysine, Eudragit E, diethanolamine, glycine, citrate, acetate, histidine, N-methyl glucamine, or tris(hydroxymethyl)aminomethane, or a mixture thereof). Desirably, the pH neutralizing agent has a pKa of from 2.5 to 9.5 (e.g., a pKa of 2±0.5, 2.5±1, 3±1.5, 4±2, 5±2, 6±2, 7±1, or a pKa of from 4.5 to 8.5). In certain embodiments, the pH neutralizing agent is an organic base having a pKa of 5±2. One of skill in the art will recognize that pKa values refer to pKa in water at room temperature. In other embodiments, the pH neutralizing agent is pyridoxine.

Other Excipients

A sweetener, flavoring agent and/or odorant can be added to the unit dosage forms of the invention to make them more palatable. At least one flavoring agent or odorant composition may be used. Any effective flavor or odor may be rendered. The flavoring agents may be natural, artificial, or a mixture thereof. The flavoring agent gives a flavor that is will help to reduce the undesirable taste of the active ingredient. In one embodiment, the flavoring agent may give the flavor of mint, menthol, honey lemon, orange, lemon lime, grape, cranberry, vanilla berry, bubble gum, or cherry. The flavoring agent can be natural or artificial sweetener, such as sucrose, Magnasweet™, sucralose, xylitol, sodium saccharin, cyclamate, aspartame, acesulfame, and salts thereof. In some embodiments, the sweetener is sucralose.

Acid addition salts of apomorphine may be susceptible to oxidative degradation; while their susceptibility is lower than that of apomorphine in neutral form, inclusion of preservatives (e.g., antioxidants) is desirable to prolong the shelf life of the pharmaceutical unit dosage form of the invention. Antioxidants that can be used in the pharmaceutical unit dosage forms of the invention can be selected from the group consisting of thiols (e.g., aurothioglucose, dihydrolipoic acid, propylthiouracil, thioredoxin, glutathione, cysteine, cystine, cystamine, thiodipropionic acid), sulphoximines (e.g., buthionine-sulphoximines, homo-cysteine-sulphoximine, buthionine-sulphones, and penta-, hexa- and heptathionine-sulphoximine), metal chelators (e.g, α-hydroxy-fatty acids, palmitic acid, phytic acid, lactoferrin, citric acid, lactic acid, and succinic acid, malic acid, humic acid, bile acid, bile extracts, bilirubin, biliverdin, EDTA, EGTA, and DTPA and salts thereof), sodium metabisulfite, sodium thiosulfate, vitamins and vitamin derivatives (e.g., vitamin E, vitamin C, ascorbyl palmitate, Mg ascorbyl phosphate, and ascorbyl acetate), phenols (e.g., butylhydroxytoluene, butylhydroxyanisole, ubiquinol, nordihydroguaiaretic acid, trihydroxybutyrophenone), benzoates (e.g., coniferyl benzoate), uric acid, mannose, propyl gallate, selenium (e.g., selenium-methionine), stilbenes (e.g., stilbene oxide and trans-stilbene oxide), and combinations thereof. The total amount of antioxidant included in the films can be from 0.001% to 3% (w/w). In certain embodiments, the antioxidant is EDTA or a salt thereof, or sodium metabisulfite, or a mixture thereof.

The films of the invention can include from 1 to 50% (w/w) of one or more hydrolyzed starches. Various hydrolyzed starches may be utilized including maltrodextrins with a DE greater than 10 and dried glucose syrups which have a DE above 20. Suitable hydrolyzed starch products are commercially available from Grain Processing Corporation of Muscatine, Iowa under trademarks such as MALTRIN M200®, MALTRIN 180®, and MALTRIN 250®. MALTRIN M200® is a hydrolyzed starch product having a DE of 20, and MALTRIN 180® is a hydrolyzed starch product having a DE of 18. Dextrose equivalent (DE) is the relative sweetness of sugars, oligosaccharides, or blends compared to dextrose, both expressed as a percentage. For example, a maltodextrin with a DE of 10 would be 10% as sweet as dextrose (DE=100), while sucrose, with a DE of 120, would be 1.2 times as sweet as dextrose. For solutions made from starch, it is an estimate of the percentage reducing sugars present in the total starch product. The DE describes the degree of conversion of starch to dextrose: starch is close to 0, glucose/dextrose is 100 (percent), dextrins vary between 1 and 13, and maltodextrins vary between 3 and 20. The DE gives an indication of the average degree of polymerisation (DP) for starch sugars. The rule of thumb is $$DE \times DP = 120.$$

In certain embodiments, the various components (e.g., plasticizers, penetration enhancers, flavoring agents, antioxidants, odorants, coloring agents, particulate base, and dopamine agonist particles) included in the unit dosage forms of the invention can be combined and incorporated into a first portion that is acidic and includes the acid addition salt of apomorphine, or combined and incorporated into a second portion that includes a pH neutralizing component, or the components may be divided between the two portions. In some instances it may be desirable to minimize interaction between the acidic portion of the unit dosage form and the basic portion of the unit dosage form by including a barrier between the two. In some pharmaceutical unit dosage forms, a barrier can be included between the first portion and the second portion. For example, when the portions are layers, the barrier can be a third layer interposed between the first portion (first layer) and the second portion (second layer). Alternatively, the barrier can be a rapidly dissolving coating on the surface of a particulate component in the unit dosage form, such as a coated particulate base coated onto, or embedded within, a first portion of the unit dosage form. In still another approach, the barrier can be a rapidly dissolving coating on the surface of apomorphine particles in the unit dosage form. These approaches can be utilized to ensure that the acid addition salt of apomorphine in the first portion of the unit dosage form is not neutralized prior to the administration to a subject.

Apomorphine

Pharmaceutical unit dosage forms of the invention include an acid addition salt of apomorphine. Examples of acids that may be used in acid addition salts of apomorphine include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids; polymeric acids such as tannic acid, carboxymethyl cellulose, or alginic acid; and inorganic acid such as hydrochloric acid, hydrobromic acid, sulfuric acid, or phosphoric acid. In some embodiments, the acid addition salt of apomorphine is apomorphine hydrochloride. A pharmaceutical unit dosage form of the invention may contain from 2 mg to 60 mg of an acid addition salt of apomorphine (e.g., from 8 mg to 45 mg of an acid addition salt of apomorphine). Certain exemplary pharmaceutical unit dosage forms may contain 10.0±2.0 mg, 12.5±2.5 mg, 15.0±2.5 mg, 17.5±2.5 mg, 20.0±5.0 mg, 25.0±5.0 mg, 30.0±10.0 mg, 30.0±5.0 mg, 35.0±10.0 mg, or 35.0±5.0 mg of an acid addition salt of apomorphine. The first portion may contain from 20% (w/w) to 60% (w/w) of an acid addition salt of apomorphine (e.g., from 30% (w/w) to 60% (w/w) or from 40% (w/w) to 60% (w/w)) relative to the weight of the dry first portion. In particular, the film may contain 50±10% (w/w) (e.g., 54±10% (w/w)) or an acid addition salt of apomorphine. Despite high content of an acid addition salt of apomorphine, the pharmaceutical unit dosage forms of the invention can exhibit toughness as described herein. The desirable toughness of the pharmaceutical unit dosage forms of the invention can be achieved, e.g., as described herein.

The pharmaceutical unit dosage forms described herein can include apomorphine microparticles having a D50 of from 1 μm to 500 μm (e.g., from 1 μm to 100 μm or 1 μm to 50 μm). The starting microparticles can be microspheres can be made of an acid addition salt of apomorphine and predominantly crystalline, predominantly microcrystalline, predominantly amorphous, or a mixture thereof. An acid addition salt of apomorphine can be encapsulated in the microsphere or included in a dissolved-drug microsphere.

In an alternative approach, the pharmaceutical formulations described herein can include apomorphine particles having an effective particle size of less than about 1 μm (i.e., nanoparticulate formulations). The starting microparticles can be microspheres can be made of an acid addition salt of apomorphine and predominantly crystalline, predominantly microcrystalline, predominantly amorphous, or a mixture thereof. An acid addition salt of apomorphine can be encapsulated in the microsphere or included in a dissolved-drug microsphere.

These apomorphine particles can be made by using any method known in the art for achieving the desired particle sizes. Useful methods include, for example, milling, homogenization, supercritical fluid fracture, or precipitation techniques. Exemplary methods are described in U.S. Pat. Nos. 4,540,602; 5,145,684; 5,518,187; 5,718,388; 5,862,999; 5,665,331; 5,662,883; 5,560,932; 5,543,133; 5,534,270; and U.S. Pat. Nos. 5,510,118; 5,470,583, each of which is specifically incorporated by reference.

The following examples are meant to illustrate the invention. They are not meant to limit the invention in any way.

EXAMPLES

Example 1

Two Layer Apomorphine Film

Preparation of the Solid Solution Layer:

Sodium metabisulfite, disodium EDTA, propylene glycol, disintegrant, and sucralose are added to water and the mixture stirred. Acetone and menthol are then added to this solution, and the mixture stirred. Apomorphine hydrochloride is added to the mixture with stirring, forming a clear solution. Polysaccharide is then added slowly with stirring. The resultant mixture is placed under vacuum to eliminate air bubbles, cast as a uniform layer unto an inert support, and then dried in an oven to produce a film comprising a solid solution of apomorphine hydrochloride.

Preparation of the Particulate Layer:

Ethyl cellulose, poly(ethylene oxide), and hydroxypropylcellulose are dissolved in a solvent (e.g., water/acetone) to form a solution.

Particulate apomorphine hydrochloride is prepared by milling solid apomorphine hydrochloride as described herein.

The particulate apomorphine hydrochloride is suspended in the solution and a solvent-cast mucoadhesive film is prepared by casting a thin film of the mixture onto a sheet. Evaporation of the solvent (e.g., water/acetone) can be accomplished by drying at 60° C. for 30 minutes producing a film.

Preparation of the Bi-Layer Film.

The 2 layers are laminated together by applying a spray of a solvent (e.g., ethanol) between them and then drying them in an oven to form the final bi-layer film. The resultant dry bilayer film includes (i) a first layer containing a rapid release solid solution of apomorphine hydrochloride and a slow release apomorphine hydrochloride particles, and (ii) a second layer that contains a buffer (e.g., an organic base, such as pyridoxine).

The two layer film can be made to optimize its efficacy per unit dosage for individual PD patients based on their therapeutic window, while simultaneously minimizing its toxicity per unit dosage.

The two-layer film is cut into strips, each strip containing the equivalent of from 2 mg to 60 mg of apomorphine (free base mass). The strips can be administered to a subject for the treatment of Parkinson's disease. The mole ratio of solid solution apomorphine to microparticulate apomorphine in the final dosage form can be controlled by varying the amount of apomorphine included in each layer and/or by controlling the relative size of each layer incorporated into the final dosage form. The ration can be from 1:9 to 9:1; 1:9 to 1:1, 1:1 to 9:1, 1:7 to 7:1; 1:7 to 1:1, 1:1 to 7:1, 1:5 to 5:1; 1:5 to 1:1, 1:1 to 5:1, 1:4 to 4:1; 1:4 to 1:1, or 1:1 to 4:1.

Example 2

Tri-Layer Apomorphine Film

A first layer containing a rapid release solid solution of apomorphine hydrochloride, and a second layer that contains a slow release apomorphine hydrochloride particles are prepared as described in Example 1.

Preparation of the pH Neutralizing

Ethyl cellulose, poly(ethylene oxide), and hydroxypropylcellulose are dissolved in anhydrous ethanol to form a solution. To the resulting solution is added a pH modifying agent (i.e., pyridoxine).

A solvent-cast mucoadhesive film is prepared by casting a thin film of the solution onto the first layer. Evaporation of the solvent (ethanol) can be accomplished by drying at 60° C. for 30 minutes.

Preparation of a Tri-Layer Film

The 3 layers may be laminated together by applying a spray of ethanol between each pair of layers, assembling them as desired, and then drying them in an oven to form the final tri-layer film. The resultant dry tri-layer film includes (i) a first layer containing a rapid release solid solution of apomorphine hydrochloride, (ii) a second layer that contains a slow release apomorphine hydrochloride particles, and (iii) a third layer that contains a pH neutralizing agent.

The three layer film can provide effect treatment for a range of therapeutic windows in patients that typically display moderate to low responsiveness for conventional drugs, while reducing the frequency or intensity of the related adverse effects. Furthermore, the three layer film can enhance the bioavailability of the apomorphine, as absorption is enhanced when apomorphine hydrochloride is neutralized, without compromising the shelf life stability of the film.

The three-layer film can cut into strips, each strip containing the equivalent of from 2 mg to 100 mg of apomorphine (free base mass). The strips can be administered to a subject for the treatment of Parkinson's disease. The mole ratio of solid solution apomorphine to microparticulate apomorphine in the final dosage form can be controlled by varying the amount of apomorphine included in each of the first and second layers and/or by controlling the relative size of each of the first and second layers incorporated into the final dosage form. The ration can be from 1:9 to 9:1; 1:9 to 1:1, 1:1 to 9:1, 1:7 to 7:1; 1:7 to 1:1, 1:1 to 7:1, 1:5 to 5:1; 1:5 to 1:1, 1:1 to 5:1, 1:4 to 4:1; 1:4 to 1:1, or 1:1 to 4:1.

Example 3

Single Layer Apomorphine Film Coated with Apomorphine Particulates

A first layer containing a rapid release solid solution of apomorphine hydrochloride is prepared as described in Example 1. The resultant dry film includes a single adhesive layer that is made of a rapid release solid solution of apomorphine hydrochloride. A surface of the film is coated with particulate apomorphine hydrochloride.

The particle-coated film can be cut into strips, each strip containing the equivalent of from 2 mg to 100 mg of apomorphine (free base mass). The strips can be administered to a subject for the treatment of Parkinson's disease.

The mole ratio of solid solution apomorphine to microparticulate apomorphine in the final dosage form can be controlled by varying the amount of apomorphine included in the rapid release layer and/or by controlling the amount of particulate apomorphine added to the first layer. The ratio can be from 1:9 to 9:1; 1:9 to 1:1, 1:1 to 9:1, 1:7 to 7:1; 1:7 to 1:1, 1:1 to 7:1, 1:5 to 5:1; 1:5 to 1:1, 1:1 to 5:1, 1:4 to 4:1; 1:4 to 1:1, or 1:1 to 4:1.

Example 4

Two Layer Apomorphine Film

Apomorphine hydrochloride layers of Films A-M were prepared by adding a high molecular weight polymer (e.g., hydroxyethyl cellulose, such as Natrosol 250G or Natrosol 250L) and, optionally, a low molecular weight polymer (e.g., hypromellose, such as Methocel E5; or hydroxypropyl cellulose, such as Nisso SSL HPC) to water with stirring until a uniform, clear, viscous liquid was produced. Sodium metabisulfite, disodium EDTA dehydrate, glycerin, maltodextrin (e.g., maltodextrin M180), and sucralose were then all added, and the mixture was stirred. Acetone and, optionally, glyceryl monostearate and menthol were added to this solution, and the mixture was stirred. Apomorphine hydrochloride was added with stirring, forming an opaque dispersion. The resulting mixture was placed under vacuum to eliminate air bubbles, cast as a uniform layer onto an inert support, and dried in an oven. The film appearances are provided below.

Pyridoxine layers of Films A-K were prepared by adding a high molecular weight polymer (e.g., hydroxyethyl cellulose, such as Natrosol 250G or Natrosol 250L) and, optionally, a low molecular weight polymer (e.g., hypromellose, such as Methocel E5; or hydroxypropyl cellulose, such as Nisso SSL HPC) to water with stirring until a uniform, clear, viscous liquid was produced. Sodium hydroxide, pyridoxine hydrochloride, sodium metabisulfite, disodium EDTA dehydrate, glycerin, maltodextrin (e.g., maltodextrin M180), and, optionally, sucralose were then all added, and the mixture was stirred. Acetone and, optionally, glyceryl monostearate and menthol were added to this solution, and the mixture was stirred, until a uniform, clear, viscous liquid was produced. The resulting mixture was placed under vacuum to eliminate air bubbles. The viscous liquid was then cast as a uniform layer onto an inert support and dried in an oven.

The separate apomorphine hydrochloride layer and pyridoxine layer were laminated together by applying a spray of ethanol between them. This bilayer construction, sandwiched between two inert supports, was dried in an oven. The dried bilayer was removed from the inert supports, cut into unit-dose films.

All films were prepared using a solid particulate apomorphine hydrochloride. Nitrogen was used as the process gas at a pressure of 100 PSI and temperature of 25-45° C. The quantities of the solid ingredients are provided in Tables A1-L2. Film M has the same proportions of the ingredients as films D-F, except for apomorphine hydrochloride, of which 3 mg per dry film were used.

Film A

TABLE A1

| Component | Dry film (mg/100 mg) | Dry film (mg) |
|---|---|---|
| sodium metabisulfite | 1.73 | 0.423 |
| disodium EDTA dihydrate | 1.73 | 0.423 |
| apomorphine hydrochloride | 12.27 | 3 |
| menthol | 7.24 | 1.77 |
| glyceryl monostearate | 1.03 | 0.252 |
| glycerin | 6.01 | 1.47 |
| maltodextrin M180 | 31.13 | 7.61 |
| sucralose | 4.44 | 1.09 |
| Natrosol 250 L | 32.87 | 8.04 |
| Methocel E5 | 1.55 | 0.379 |
| Total mass (mg) | 100 | 24.457 |

The dried apomorphine hydrochloride layer was transparent in appearance containing the dissolved drug.

TABLE A2

| Component | Dry film (mg/100 mg) | Dry film (mg) |
|---|---|---|
| pyridoxine hydrochloride | 8.107 | 1.63 |
| sodium hydroxide | 1.62 | 0.326 |
| sodium metabisulfite | 1.847 | 0.371 |
| disodium EDTA dihydrate | 1.853 | 0.373 |
| glycerin | 5.54 | 1.11 |
| maltodextrin M180 | 33.49 | 6.73 |
| Natrosol 250 L | 34.18 | 6.87 |
| glyceryl monostearate | 1.054 | 0.212 |
| menthol | 7.739 | 1.56 |
| sucralose | 4.569 | 0.919 |
| Total Mass (mg) | 100 | 20.101 |

Film B

TABLE B1

| Component | Dry film (mg/100 mg) | Dry film (mg) |
|---|---|---|
| sodium metabisulfite | 1.899 | 0.711 |
| disodium EDTA dihydrate | 1.895 | 0.709 |
| apomorphine hydrochloride | 21.38 | 8 |
| menthol | 4.814 | 1.8 |
| glyceryl monostearate | 1.202 | 0.45 |
| glycerin | 3.332 | 1.25 |
| maltodextrin M180 | 40.27 | 15.1 |
| sucralose | 1.869 | 0.699 |
| Natrosol 250 L | 22.27 | 8.33 |
| Methocel E5 | 1.067 | 0.399 |
| Total mass (mg) | 100 | 37.448 |

The dried apomorphine hydrochloride layer was translucid in appearance containing the dissolved and undissolved drug.

TABLE B2

| Component | Dry film (mg/100 mg) | Dry film (mg) |
|---|---|---|
| pyridoxine hydrochloride | 59.32 | 15.3 |
| sodium hydroxide | 9.989 | 2.58 |
| sodium metabisulfite | 0.4105 | 0.106 |
| disodium EDTA dihydrate | 0.3704 | 0.09055 |
| glycerin | 1.942 | 0.501 |
| maltodextrin M180 | 2.317 | 0.598 |
| Natrosol 250 L | 25.65 | 6.62 |
| Total Mass (mg) | 100 | 25.796 |

Film C

TABLE C1

| Component | Dry film (mg/100 mg) | Dry film (mg) |
|---|---|---|
| sodium metabisulfite | 1.708 | 0.711 |
| disodium EDTA dihydrate | 1.712 | 0.712 |
| apomorphine HCL | 28.84 | 12 |
| menthol | 4.81 | 2 |
| glyceryl monostearate | 1.082 | 0.45 |
| glycerin | 3.005 | 1.25 |
| maltodextrin M180 | 36.18 | 15.1 |
| sucralose | 1.68 | 0.699 |
| Natrosol 250 L | 20.02 | 8.33 |
| Methocel E5 | 0.963 | 0.401 |
| Total mass (mg) | 100 | 41.653 |

The dried apomorphine hydrochloride film was translucid in appearance containing the dissolved and undissolved drug.

TABLE C2

| Component | Dry film (mg/100 mg) | Dry film (mg) |
|---|---|---|
| pyridoxine hydrochloride | 59.32 | 15.3 |
| sodium hydroxide | 9.989 | 2.58 |
| sodium metabisulfite | 0.4105 | 0.106 |
| disodium EDTA dihydrate | 0.3704 | 0.09055 |
| glycerin | 1.942 | 0.501 |

TABLE C2-continued

| Component | Dry film (mg/100 mg) | Dry film (mg) |
|---|---|---|
| maltodextrin M180 | 2.317 | 0.598 |
| Natrosol 250 L | 25.65 | 6.62 |
| Total Mass (mg) | 100 | 25.796 |

Film D

TABLE D1

| Component | Dry film (mg/100 mg) | Dry film (mg) |
|---|---|---|
| sodium metabisulfite | 1.532 | 0.711 |
| disodium EDTA dihydrate | 1.534 | 0.712 |
| apomorphine hydrochloride | 53.851 | 25 |
| menthol | 4.954 | 2.3 |
| glyceryl monostearate | 0.485 | 0.225 |
| glycerin | 7.486 | 3.475 |
| maltodextrin M180 | 23.067 | 10.709 |
| sucralose | 1.506 | 0.699 |
| Natrosol 250 G | 3.279 | 1.522 |
| Nisso SSL HPC | 2.234 | 1.037 |
| FD&C Blue | 0.072 | 0.033 |
| Total mass (mg) | 100 | 46.423 |

The dried apomorphine hydrochloride layer was opaque in appearance containing dissolved and undissolved drug.

TABLE D2

| Component | Dry film (mg/100 mg) | Dry film (mg) |
|---|---|---|
| pyridoxine hydrochloride | 73.73 | 18 |
| sodium hydroxide | 12.24 | 3.035 |
| sodium metabisulfite | 0.4352 | 0.108 |
| disodium EDTA dihydrate | 0.3795 | 0.0939 |
| glycerin | 0.1367 | 0.0338 |
| maltodextrin M180 | 2.027 | 0.502 |
| glyceryl monostearate | 0.8204 | 0.203 |
| menthol | 0.4044 | 0.1 |
| sucralose | 0.4103 | 0.102 |
| Natrosol 250 G | 6.164 | 1.53 |
| Nisso SSL HPC | 4.189 | 1.04 |
| FD&C Blue #1 | 0.06161 | 0.0167 |
| Total Mass (mg) | 100 | 24.75 |

Film E

TABLE E1

| Component | Dry film (mg/100 mg) | Dry film (mg) |
|---|---|---|
| sodium metabisulfite | 1.532 | 0.4266 |
| disodium EDTA dihydrate | 1.534 | 0.4272 |
| apomorphine hydrochloride | 53.851 | 15 |
| menthol | 4.954 | 1.38 |
| glyceryl monostearate | 0.485 | 0.135 |
| glycerin | 7.486 | 2.085 |
| maltodextrin M180 | 23.067 | 6.425 |
| sucralose | 1.506 | 0.4194 |
| Natrosol 250 G | 3.279 | 0.9132 |
| Nisso SSL HPC | 2.234 | 0.6222 |
| FD&C Blue | 0.072 | 0.02 |
| Total mass (mg) | 100 | 27.854 |

The dried apomorphine hydrochloride layer was opaque in appearance containing dissolved and undissolved drug.

TABLE E2

| Component | Dry film (mg/100 mg) | Dry film (mg) |
|---|---|---|
| pyridoxine hydrochloride | 73.73 | 11 |
| sodium hydroxide | 12.24 | 1.855 |
| sodium metabisulfite | 0.4352 | 0.0648 |
| disodium EDTA dihydrate | 0.3795 | 0.0556 |
| glycerin | 0.1367 | 0.0207 |
| maltodextrin M180 | 2.027 | 0.307 |
| glyceryl monostearate | 0.8204 | 0.124 |
| menthol | 0.4044 | 0.0612 |
| sucralose | 0.4103 | 0.621 |
| Natrosol 250 G | 6.164 | 0.932 |
| Nisso SSL HPC | 4.189 | 0.634 |
| FD&C Blue #1 | 0.06161 | 0.0102 |
| Total Mass (mg) | 100 | 15.125 |

Film F

TABLE F1

| Component | Dry film (mg/100 mg) | Dry film (mg) |
|---|---|---|
| sodium metabisulfite | 1.532 | 0.2844 |
| disodium EDTA dihydrate | 1.534 | 0.2848 |
| apomorphine hydrochloride | 53.851 | 10 |
| menthol | 4.954 | 0.92 |
| glyceryl monostearate | 0.485 | 0.09 |
| glycerin | 7.486 | 1.39 |
| maltodextrin M180 | 23.067 | 4.2836 |
| sucralose | 1.506 | 0.2796 |
| Natrosol 250 G | 3.279 | 0.6088 |
| Nisso SSL HPC | 2.234 | 0.4148 |
| FD&C Blue | 0.072 | 0.0132 |
| Total mass (mg) | 100 | 18.569 |

The dried apomorphine hydrochloride layer was opaque in appearance containing dissolved and undissolved drug.

TABLE F2

| Component | Dry film (mg/100 mg) | Dry film (mg) |
|---|---|---|
| pyridoxine hydrochloride | 73.73 | 7.3 |
| sodium hydroxide | 12.24 | 1.23 |
| sodium metabisulfite | 0.4352 | 0.0437 |
| disodium EDTA dihydrate | 0.3795 | 0.0381 |
| glycerin | 0.1367 | 0.0137 |
| maltodextrin M180 | 2.027 | 0.203 |
| glyceryl monostearate | 0.8204 | 0.0823 |
| menthol | 0.4044 | 0.0406 |
| sucralose | 0.4103 | 0.0412 |
| Natrosol 250 G | 6.164 | 0.619 |
| Nisso SSL HPC | 4.189 | 0.42 |
| FD&C Blue #1 | 0.06161 | 0.00679 |
| Total Mass (mg) | 100 | 10.037 |

Film G

TABLE G1

| Component | Dry film (mg/100 mg) | Dry film (mg) |
|---|---|---|
| sodium metabisulfite | 1.53 | 0.85 |
| disodium EDTA dihydrate | 1.53 | 0.85 |
| apomorphine hydrochloride | 53.83 | 30 |
| menthol | 4.96 | 2.76 |

TABLE G1-continued

| Component | Dry film (mg/100 mg) | Dry film (mg) |
|---|---|---|
| glyceryl monostearate | 0.48 | 0.27 |
| glycerin | 7.52 | 4.19 |
| maltodextrin M180 | 23.05 | 12.8 |
| sucralose | 1.51 | 0.84 |
| Natrosol 250 G | 3.28 | 1.83 |
| Nisso SSL HPC | 2.23 | 1.24 |
| FD&C Blue | 0.07 | 0.004 |
| Total mass (mg) | 100 | 55.7 |

The dried apomorphine hydrochloride layer was opaque in appearance containing dissolved and undissolved drug.

TABLE G2

| Component | Dry film (mg/100 mg) | Dry film (mg) |
|---|---|---|
| pyridoxine hydrochloride | 72.73 | 21.69 |
| sodium hydroxide | 12.24 | 3.65 |
| sodium metabisulfite | 0.44 | 0.13 |
| disodium EDTA dihydrate | 0.38 | 0.11 |
| glycerin | 0.14 | 0.04 |
| maltodextrin M180 | 2.03 | 0.6 |
| glyceryl monostearate | 0.82 | 0.24 |
| menthol | 0.4 | 0.12 |
| sucralose | 0.41 | 0.12 |
| Natrosol 250 G | 6.16 | 1.84 |
| Nisso SSL HPC | 4.19 | 1.25 |
| FD&C Blue #1 | 0.07 | 0.02 |
| Total Mass (mg) | 100 | 29.82 |

Film H

TABLE H1

| Component | Dry film (mg/100 mg) | Dry film (mg) |
|---|---|---|
| sodium metabisulfite | 1.53 | 0.71 |
| disodium EDTA dihydrate | 1.53 | 0.71 |
| apomorphine hydrochloride | 53.83 | 25 |
| menthol | 4.96 | 2.3 |
| glyceryl monostearate | 0.48 | 0.22 |
| glycerin | 7.52 | 3.49 |
| maltodextrin M180 | 23.05 | 10.7 |
| sucralose | 1.51 | 0.7 |
| Natrosol 250 G | 3.28 | 1.52 |
| Nisso SSL HPC | 2.23 | 1.04 |
| FD&C Blue | 0.07 | 0.03 |
| Total mass (mg) | 100 | 46.44 |

The dried apomorphine hydrochloride layer was opaque in appearance containing dissolved and undissolved drug.

TABLE H2

| Component | Dry film (mg/100 mg) | Dry film (mg) |
|---|---|---|
| pyridoxine hydrochloride | 72.73 | 18.08 |
| sodium hydroxide | 12.24 | 3.04 |
| sodium metabisulfite | 0.44 | 0.11 |
| disodium EDTA dihydrate | 0.38 | 0.09 |
| glycerin | 0.14 | 0.03 |
| maltodextrin M180 | 2.03 | 0.5 |
| glyceryl monostearate | 0.82 | 0.2 |
| menthol | 0.4 | 0.1 |
| sucralose | 0.41 | 0.1 |
| Natrosol 250 G | 6.16 | 1.53 |

TABLE H2-continued

| Component | Dry film (mg/100 mg) | Dry film (mg) |
|---|---|---|
| Nisso SSL HPC | 4.19 | 1.04 |
| FD&C Blue #1 | 0.07 | 0.02 |
| Total Mass (mg) | 100 | 24.86 |

Film I

TABLE I1

| Component | Dry film (mg/100 mg) | Dry film (mg) |
|---|---|---|
| sodium metabisulfite | 1.53 | 0.57 |
| disodium EDTA dihydrate | 1.53 | 0.57 |
| apomorphine hydrochloride | 53.83 | 20 |
| menthol | 4.96 | 1.84 |
| glyceryl monostearate | 0.48 | 0.18 |
| glycerin | 7.52 | 2.79 |
| maltodextrin M180 | 23.05 | 8.56 |
| sucralose | 1.51 | 0.56 |
| Natrosol 250 G | 3.28 | 1.22 |
| Nisso SSL HPC | 2.23 | 0.83 |
| FD&C Blue | 0.07 | 0.03 |
| Total mass (mg) | 100 | 37.15 |

The dried apomorphine hydrochloride layer was opaque in appearance containing dissolved and undissolved drug.

TABLE I2

| Component | Dry film (mg/100 mg) | Dry film (mg) |
|---|---|---|
| pyridoxine hydrochloride | 72.73 | 14.46 |
| sodium hydroxide | 12.24 | 2.43 |
| sodium metabisulfite | 0.44 | 0.09 |
| disodium EDTA dihydrate | 0.38 | 0.08 |
| glycerin | 0.14 | 0.03 |
| maltodextrin M180 | 2.03 | 0.4 |
| glyceryl monostearate | 0.82 | 0.16 |
| menthol | 0.4 | 0.08 |
| sucralose | 0.41 | 0.08 |
| Natrosol 250 G | 6.16 | 1.23 |
| Nisso SSL HPC | 4.19 | 0.83 |
| FD&C Blue #1 | 0.07 | 0.01 |
| Total Mass (mg) | 100 | 19.89 |

Film J

TABLE J1

| Component | Dry film (mg/100 mg) | Dry film (mg) |
|---|---|---|
| sodium metabisulfite | 1.53 | 0.43 |
| disodium EDTA dihydrate | 1.53 | 0.43 |
| apomorphine hydrochloride | 53.83 | 15 |
| menthol | 4.96 | 1.38 |
| glyceryl monostearate | 0.48 | 0.13 |
| glycerin | 7.52 | 2.09 |
| maltodextrin M180 | 23.05 | 6.42 |
| sucralose | 1.51 | 0.42 |
| Natrosol 250 G | 3.28 | 0.91 |
| Nisso SSL HPC | 2.23 | 0.62 |
| FD&C Blue | 0.07 | 0.02 |
| Total mass (mg) | 100 | 27.86 |

The dried apomorphine hydrochloride layer was opaque in appearance containing dissolved and undissolved drug.

TABLE J2

| Component | Dry film (mg/100 mg) | Dry film (mg) |
| --- | --- | --- |
| pyridoxine hydrochloride | 72.73 | 10.85 |
| sodium hydroxide | 12.24 | 1.83 |
| sodium metabisulfite | 0.44 | 0.06 |
| disodium EDTA dihydrate | 0.38 | 0.06 |
| glycerin | 0.4 | 0.06 |
| maltodextrin M180 | 2.03 | 0.3 |
| glyceryl monostearate | 0.82 | 0.12 |
| menthol | 0.4 | 0.06 |
| sucralose | 0.41 | 0.06 |
| Natrosol 250 G | 6.16 | 0.92 |
| Nisso SSL HPC | 4.19 | 0.62 |
| FD&C Blue #1 | 0.07 | 0.01 |
| Total Mass (mg) | 100 | 14.92 |

Film K

TABLE K1

| Component | Dry film (mg/100 mg) | Dry film (mg) |
| --- | --- | --- |
| sodium metabisulfite | 1.53 | 0.28 |
| disodium EDTA dihydrate | 1.53 | 0.28 |
| apomorphine hydrochloride | 53.83 | 10 |
| menthol | 4.96 | 0.92 |
| glyceryl monostearate | 0.48 | 0.09 |
| glycerin | 7.52 | 1.4 |
| maltodextrin M180 | 23.05 | 4.28 |
| sucralose | 1.51 | 0.28 |
| Natrosol 250 G | 3.28 | 0.61 |
| Nisso SSL HPC | 2.23 | 0.41 |
| FD&C Blue | 0.07 | 0.01 |
| Total mass (mg) | 100 | 18.58 |

The dried apomorphine hydrochloride layer was opaque in appearance containing dissolved and undissolved drug.

TABLE K2

| Component | Dry film (mg/100 mg) | Dry film (mg) |
| --- | --- | --- |
| pyridoxine hydrochloride | 72.73 | 7.23 |
| sodium hydroxide | 12.24 | 1.22 |
| sodium metabisulfite | 0.44 | 0.04 |
| disodium EDTA dihydrate | 0.38 | 0.04 |
| glycerin | 0.14 | 0.01 |
| maltodextrin M180 | 2.03 | 0.2 |
| glyceryl monostearate | 0.82 | 0.08 |
| menthol | 0.4 | 0.04 |
| sucralose | 0.41 | 0.04 |
| Natrosol 250 G | 6.16 | 0.61 |
| Nisso SSL HPC | 4.19 | 0.42 |
| FD&C Blue #1 | 0.07 | 0.01 |
| Total Mass (mg) | 100 | 9.94 |

Film L

TABLE L1

| Component | Dry film (mg/100 mg) |
| --- | --- |
| sodium metabisulfite | 1.619 |
| disodium EDTA dihydrate | 1.621 |
| apomorphine hydrochloride | 53.83 |
| Glycerin | 4.770 |
| maltodextrin M180 | 9.12 |
| Sucralose | 1.600 |
| Natrosol 250 G | 7.797 |
| Natrosol 250 L | 17.203 |
| Nisso SSL HPC | 2.362 |
| FD&C Blue #1 | 0.07581 |
| Total mass (mg) | 100 |

The dried apomorphine hydrochloride layer was opaque in appearance containing the dissolved and undissolved drug.

TABLE L2

| Component | Dry film (mg/100 mg) |
| --- | --- |
| pyridoxine hydrochloride | 67.54 |
| sodium hydroxide | 11.37 |
| sodium metabisulfite | 0.4239 |
| disodium EDTA dihydrate | 0.3696 |
| glycerin | 0.1331 |
| maltodextrin M180 | 0.400 |
| Sucralose | 0.400 |
| Natrosol 250 L | 15.50 |
| FD&C Blue #1 | 0.06585 |
| Total Mass (mg) | 100 |

Film M

Film M was prepared according to the same procedure as that described for films D-F with the exception of including only 3 mg of apomorphine hydrochloride per 100 mg of dry film. Film M was entirely transparent containing fully dissolved apomorphine hydrochloride. The solubility of apomorphine in the films appears to be somewhere between 3 and 7 mg per film.

Example 5

Pharmacokinetics (PK)

Film A

In Period 1, Film A was placed on underside of tongue, drug layer away from tissue. In Period 2, the drug was placed on underside of tongue, drug layer toward the tissue.

Tables 1 and 2 below provide the non-compartmental PK results obtained using WinNonlin (Bill Wargin, ClinPharm Consulting, RTP, NC) and PK values from Apokyn® NDA 21-264 (study APO-0083). Table 1 shows the results of Period 1. Table 2 shows Period 2 results. In Period 1, four subjects had anomalous half-life values and could not be used in the calculations, limiting the analysis to n=8 for certain PK parameters strongly influenced by the elimination phase. In Period 2, one subject's plasma profile was deemed in error (Subject #13) due to a very anomalous PK profile and a Tmax result that was >25D outside the norm. It is believed that the sample set may have been inverted and PK-AE correlations might support that assumption. PK determinations were performed with and without Subject #13 inclusion. Removing Subject #13 does not significantly change the other PK parameters, but has a significant impact on the calculated value of Tmax.

TABLE 1

| Parameter | Cmax (ng/mL) | Tmax (min) | t½ (min) | AUClast (min * ng/mL) | AUCinf (min * ng/mL) | CL/F (L/min/kg) | Vz/F (L/kg) |
|---|---|---|---|---|---|---|---|
| Period 1 | | | | | | | |
| N (male) | 12 | 12 | 8 | 12 | 8 | 8 | 8 |
| Mean | 0.933 | 64.2 | 51.3 | 63.1 | 82.5 | 0.883 | 67.7 |
| SD | 0.777 | 61.1 | 26.3 | 40.1 | 35.8 | 0.436 | 57.1 |
| Min | 0.105 | 10.0 | 19.8 | 11.2 | 35.0 | 0.460 | 25.7 |
| Median | 0.804 | 52.5 | 45.0 | 56.3 | 82.2 | 0.757 | 41.5 |
| Max | 2.43 | 240.0 | 102 | 120 | 130 | 1.71 | 169 |
| CV % | 83.3 | 95.2 | 51.3 | 63.7 | 43.3 | 49.4 | 84.4 |

TABLE 2

| Parameter | Cmax (ng/mL) | Tmax (min) | t½ (min) | AUClast (min * ng/mL) | AUCinf (min * ng/mL) | CL/F (L/min/kg) | Vz/F (L/kg) |
|---|---|---|---|---|---|---|---|
| Period 2 (all Subjects) | | | | | | | |
| N (male) | 12 | 12 | 12 | 12 | 12 | 12 | 12 |
| Mean | 1.51 | 33.3 | 53.6 | 94.5 | 97.6 | 0.703 | 54.0 |
| SD | 0.817 | 29.9 | 17.6 | 36.7 | 36.7 | 0.272 | 25.4 |
| Min | 0.460 | 10.0 | 15.9 | 45.2 | 48.5 | 0.383 | 11.4 |
| Median | 1.28 | 20.0 | 51.3 | 85.9 | 89.0 | 0.674 | 48.7 |
| Max | 2.82 | 120.0 | 83.0 | 153 | 157 | 1.24 | 105 |
| CV % | 54.2 | 89.8 | 32.8 | 38.8 | 37.6 | 38.7 | 47.1 |
| Period 2 (minus Subject #13) | | | | | | | |
| N (male) | 11 | 11 | 11 | 11 | 11 | 11 | 11 |
| Mean | 1.59 | 25.5 | 54.4 | 97.7 | 101 | 0.683 | 53.5 |
| SD | 0.797 | 12.9 | 18.2 | 36.6 | 36.9 | 0.276 | 26.6 |
| Min | 0.460 | 10.0 | 15.9 | 45.2 | 48.5 | 0.383 | 11.4 |
| Median | 1.36 | 20.0 | 53.8 | 87.2 | 90.5 | 0.663 | 46.0 |
| Max | 2.82 | 60.0 | 83.0 | 153 | 157 | 1.24 | 105 |
| CV % | 50.1 | 50.8 | 33.4 | 37.5 | 36.7 | 40.4 | 49.7 |

Comparing Periods 1 and 2, Period 2, which has the drug layer in direct contact with the sublingual tissue of the tongue, has higher Cmax, AUClast and AUCinf parameters, as well as a shorter Tmax value. Based on the relative bioavailability (with Apokyn® set to 100% as per literature), the relative bioavailability of Period 2 is 16%.

The PK parameters for Apokyn® are provided in Table 3,

TABLE 3

| Parameter | Cmax (ng/mL) | Tmax (min) | t½ min) | AUClast (min * ng/mL) | AUCinf (min * ng/mL) | CL/F (L/min/kg) | Vz/F (L/kg) |
|---|---|---|---|---|---|---|---|
| Apokyn ® | 10.35 | 26.6 | 40.1 | 603.6 | 654 | | |
| Period 1 (N = 8) | 0.933 | 64.2 | 51.3 | 63.1 | 82.5 | 0.883 | 67.7 |
| Period 2 (N = 12) | 1.51 | 33.3 | 53.6 | 94.5 | 97.6 | 0.703 | 54.0 |
| Period 2 (N = 11) | 1.59 | 25.5 | 54.4 | 97.7 | 101 | 0.683 | 53.5 |
| Comparison | | | | | | | |
| Period 1/Ref | 9% | 244% | — | 10% | 13% | — | — |
| Period 2/Ref | 15% | 96% | — | 16% | 15% | — | — |

Film B

This study was a 2-cohort dose escalation study starting with a dose of 8 mg (Film B) and finishing with a 12 mg (Film C) dose. Within each cohort, there was a crossover design to test the orientation of the dose with the drug place under the tongue. In Treatment 1, the bilayer film was placed in the bottom of the mouth with the drug layer facing the floor of the mouth (F-Down). The next day, for Treatment 2, the bilayer was placed on the bottom side of the tongue with the drug layer facing the tongue (T-Up). Between the 2 cohorts, there was a PK and safety evaluation.

It should be noted that there was an amendment of the protocol between the 2 treatment periods of Cohort 1. Several subjects were assisted to their beds during cohort 1, due to nearly systematic adverse events of nausea, dizziness and sudden drowsiness. Thus, whereas in Treatment 1, subjects were allowed to roam the clinic after dosing and recoding of the in bucco disintegration, for Treatment 2, subjects were instructed to lie down in their beds after dosing and recoding of the in bucco disintegration and they remained throughout the next 2-3 hours of the study. The physician's evaluation of AEs attempted to make abstraction of this change in judging the severity of AEs.

Figure 2:
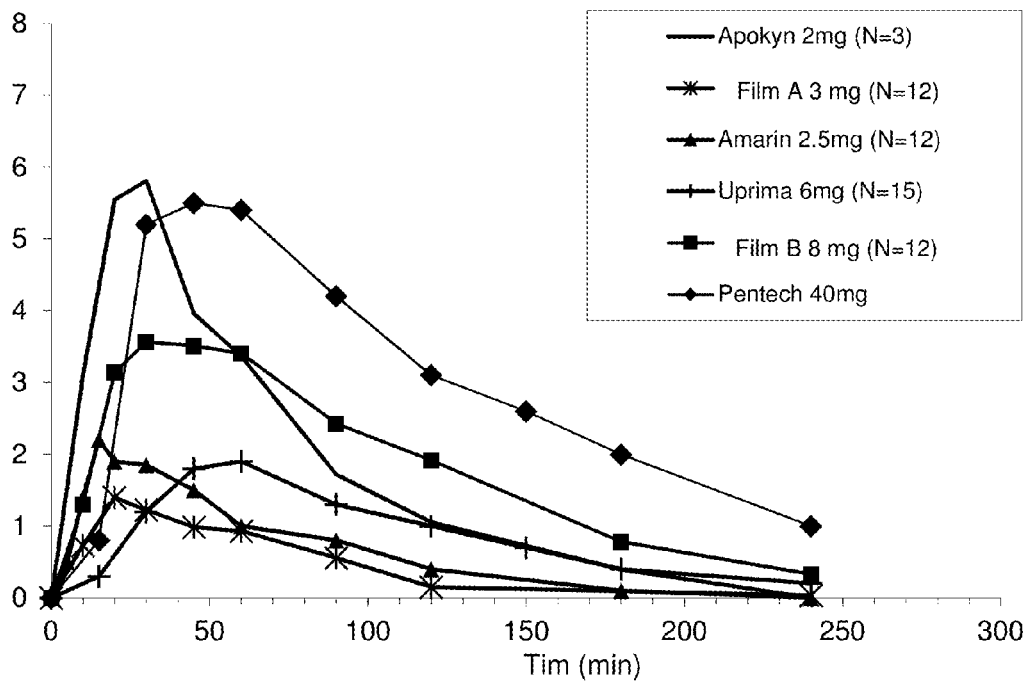
FIG. 2 is a chart showing pharmacokinetic curves for Film A, Film B, and certain previously disclosed treatments.
Figure 3:
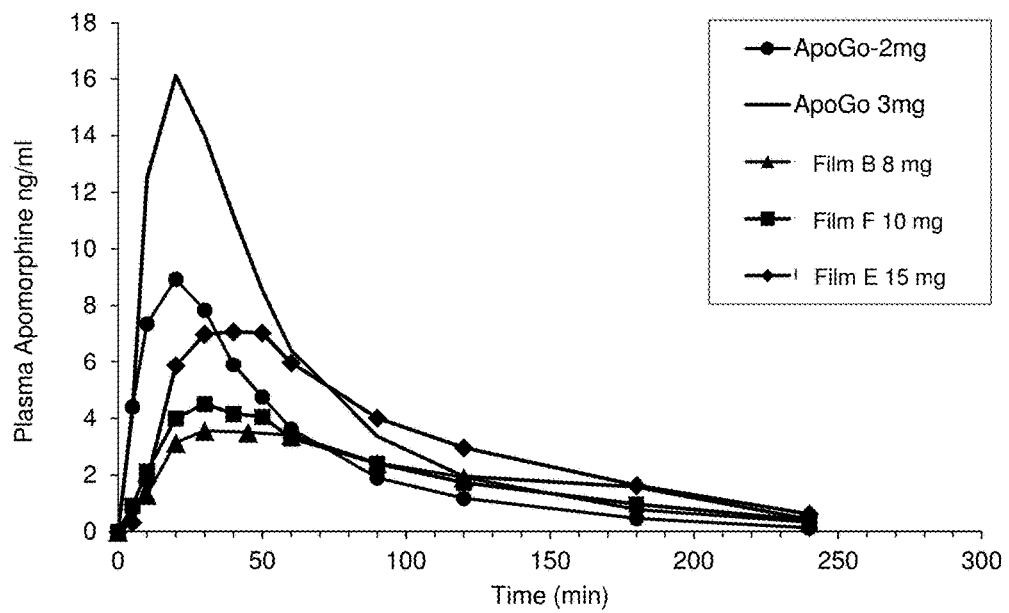
FIG. 3 is a chart showing pharmacokinetic curves for Film B, Film E, Film F, and for subcutaneous ApoGo (2 mg and 3 mg doses).

Tables 4-7 and FIGS. 1-3 include data for Film A for comparison purposes. FIG. 1 shows un-adjusted PK curves for both Film A and Film B, as well as a 2 mg curve for Apokyn®. The curve for Film B shows an increase in absorption rate and a higher Cmax than Film A. Cmax has increased proportionally from Film A. The relative bioavailability increased by 50% over Film A. Tmax remains within the 10-60 min range of Apokyn®. The curve shape is more rounded and somewhat extended on the right side at comparably adjusted AUC or Cmax for Film A.

Reference Formulation (subcutaneous (SC) ApoGo apomorphine formulation) in a randomized crossover design study. Blood samples were obtained over a 4-hour period on each dosing day, at pre-dose, and at 5, 10, 20, 30, 40, 50, 60, 90, 120, 180, and 240 minutes after dosing. Plasma apomorphine concentrations were measured using a validated LC/MS method. ApoGo is a formulation containing 10 mg of apomorphine hydrochloride and 1 mg/ml of sodium metabisulfite for subcutaneous injection.

FIG. 3 shows the PK profiles for Film B, Film E, Film F as well as for ApoGo at 2 mg dose levels. A progression to

TABLE 4

| Subject | Cmax (ng/mL) | Tmax (min) | λz (1/min) | t½ (min) | AUClast (min * ng/mL) | AUCinf (min * ng/mL) | AUCext (%) | CL/F (L/min/kg) | Vz/F (L/kg) |
|---|---|---|---|---|---|---|---|---|---|
| Film B, Treatment Period 1 F-DOWN | | | | | | | | | |
| N | 10 | 10 | 10 | 10 | 10 | 10 | 10 | 10 | 10 |
| Mean | 4.36 | 57.0 | 0.016 | 45.3 | 420 | 441 | 4.7 | 19.6 | 1260 |
| SD | 1.78 | 13.8 | 0.005 | 12.6 | 135 | 141 | 3.2 | 5.35 | 426 |
| Min | 3.03 | 45.0 | 0.010 | 25.3 | 296 | 304 | 0.5 | 10.9 | 626 |
| Median | 3.92 | 60.0 | 0.016 | 44.3 | 396 | 424 | 4.2 | 18.9 | 1320 |
| Max | 9.16 | 90.0 | 0.027 | 66.4 | 715 | 731 | 10.0 | 26.4 | 1850 |
| CV % | 40.7 | 24.2 | 30.3 | 27.8 | 32.2 | 31.9 | 69.1 | 27.3 | 33.8 |
| Film B, Treatment Period 2 T-UP | | | | | | | | | |
| N | 10 | 10 | 10 | 10 | 10 | 10 | 10 | 10 | 10 |
| Mean | 4.07 | 40.0 | 0.014 | 53.0 | 425 | 452 | 6.0 | 18.8 | 1460 |
| SD | 1.26 | 16.2 | 0.003 | 10.9 | 118 | 123 | 2.8 | 4.47 | 512 |
| Min | 2.46 | 20.0 | 0.010 | 34.7 | 302 | 326 | 1.5 | 11.7 | 744 |
| Median | 3.68 | 37.5 | 0.013 | 53.8 | 393 | 408 | 6.0 | 19.6 | 1380 |
| Max | 6.07 | 60.0 | 0.020 | 66.5 | 657 | 685 | 10.4 | 24.6 | 2160 |
| CV % | 31.1 | 40.4 | 22.7 | 20.6 | 27.8 | 27.2 | 47.7 | 23.8 | 35.2 |

TABLE 5

| Study Period | Dose mg | Orientation | Tmax min | Cmax Rel | AUCinf Rel | % CV T, C, AUC | Slope20 ng/ml/min |
|---|---|---|---|---|---|---|---|
| Film A, Period 1 | 3 | T-D | 64.2 | 11% | 14% | 43-95% | 0.027 |
| Film A, Period 2 | 3 | T-U | 25.5 | 18% | 17% | 37-51% | 0.069 |
| Film B, Period 1 | 8 | F-D | 57.0 | 19% | 26% | 32-41% | 0.125 |
| Film B, Period 2 | 8 | T-U | 40.0 | 17% | 27% | 27-40% | 0.157 |

Summary conclusions and comparisons from PK data: no lag to absorption for Film B in either orientation; T-UP orientation has faster Tmax than F-Down. Down orientation either on tongue (Film A) or in floor of mouth (Film B) clearly leads to an increase in Tmax (57-64 min); for T-UP orientation, Tmax in Film B ranges from 20-60 min with values of 20 (2), 30 (3), 45 (2), 60 (4); Tmax in Film A ranges from 10-60 min with values of 10 (1), 20 (6), 30 (3), 45 (0), 60 (1); there is a clear but modest shift to longer Tmax with Film B; and with an increase in dose from Film A (3 mg) to Film B (8 mg), there is a proportional increase in Cmax and a super-proportional increase in AUC.

Comparison of the PK data for the previously disclosed treatments with the PK data for the sublingual administration of Film A or B is shown in FIG. 2. Amarin 2.5 mg sublingual formulation results are from U.S. pre-grant publication No. 2009/0023766. Pentech 40 mg for PD formulation results are from Ondo et al., Clinical Neuropharmacology, 22:1-4, 1999.

Films E and F

Plasma concentration-time data were collected for subjects who received Test Formulation (Film B, E, or F) and higher blood levels at higher dose was observed. As can be seen in the PK determinations, these increases are proportional for both the Reference Formulation and the Test Formulations.

Reference Formulation demonstrated a Cmax of 9 ng/ml after the injection of 2 mg of API and 16 ng/ml after the injection of 3 mg of API. This is higher than was anticipated based on the Apokyn® SBA, where, in 5 different studies, mean Cmax values ranging from 5.3 to 8.1 ng/ml for 2 mg were observed, and larger studies (N=35) demonstrated Cmax 5.3-6.1 ng/ml (SBA 21-264 Study APOM-02115). The proportionality observed for both the reference and the test products suggests that the study was run under controlled conditions and methods were consistent and that the results here are not in error. The high values observed are very likely due to a combination of differences in methodology (protocol, subjects, blood handling procedures, and/or analytical methods).

Noncompartmental pharmacokinetic analysis of plasma apomorphine concentration versus time was conducted using WinNonlin Phoenix version 6.3. The analysis results are provided in Tables 6-10 below. The PK parameters for Film B are provided in Table 6 for comparison. The PK data for Film E is provided in Table 7. The PK data for Film F is provided in Table 8. Tables 9 and 10 provide PK data for 2 mg and 3 mg doses of apomorphine administered as a Reference Formulation (ApoGo), respectively.

TABLE 6

| Subject | Cmax (ng/mL) | Tmax (min) | λz (1/min) | t½ (min) | AUClast (min * ng/mL) | AUCinf (min * ng/mL) | CL/F (L/min/kg) | Vz/F** (L/kg) |
|---|---|---|---|---|---|---|---|---|
| N | 10 | 10 | 10 | 10 | 10 | 10 | 10 | 10 |
| Mean | 4.07 | 40.0 | 0.014 | 53.0 | 425 | 452 | 18.8 | 1460 |
| SD | 1.26 | 16.2 | 0.003 | 10.9 | 118 | 123 | 4.47 | 512 |
| Min | 2.46 | 20.0 | 0.010 | 34.7 | 302 | 326 | 11.7 | 744 |
| Median | 3.68 | 37.5 | 0.013 | 53.8 | 393 | 408 | 19.6 | 1380 |
| Max | 6.07 | 60.0 | 0.020 | 66.5 | 657 | 685 | 24.6 | 2160 |
| CV % | 31.1 | 40.4 | 22.7 | 20.6 | 27.8 | 27.2 | 23.8 | 35.2 |

TABLE 7

| Subject | Cmax (ng/mL) | Tmax (min) | λz (1/min) | t½ (min) | AUClast (min * ng/mL) | AUCinf (min * ng/mL) | MRT (min) |
|---|---|---|---|---|---|---|---|
| N | 12 | 12 | n.d.* | 12 | 12 | 12 | 12 |
| Mean | 8.02 | 39.2 | | 54.7 | 804 | 854 | 101 |
| SD | 2.76 | 11.6 | | 11.8 | 253 | 261 | 14.9 |
| Min | 5.23 | 20.0 | | 35.7 | 444 | 485 | 80.1 |
| Median | 8.14 | 40.0 | | 52.5 | 745 | 787 | 102 |
| Max | 14.9 | 60.0 | | 78.6 | 1395 | 1434 | 122 |
| CV % | 34.4 | 29.7 | | 21.5 | 31.5 | 30.6 | 14.7 |
| Geo mean | 7.65 | 37.5 | | 53.6 | 770 | 819 | 99.8 |

TABLE 8

| Subject | Cmax (ng/mL) | Tmax (min) | λz (1/min) | t½ (min) | AUClast (min * ng/mL) | AUCinf (min * ng/mL) | MRT (min) |
|---|---|---|---|---|---|---|---|
| N | 13 | 13 | n.d.* | 13 | 13 | 13 | 13 |
| Mean | 5.45 | 34.2 | | 56.5 | 509 | 543 | 101 |
| SD | 2.59 | 16.3 | | 15.5 | 181 | 188 | 19.8 |
| Min | 1.37 | 5.0 | | 34.9 | 156 | 167 | 55.9 |
| Median | 5.19 | 30.0 | | 58.0 | 514 | 542 | 101 |
| Max | 11.7 | 60.0 | | 93.4 | 775 | 808 | 143 |
| CV % | 47.5 | 47.6 | | 27.4 | 35.6 | 34.7 | 19.5 |
| Geo mean | 4.84 | 29.4 | | 54.7 | 472 | 505 | 99.1 |

TABLE 9

| Subject | Cmax (ng/mL) | Tmax (min) | λz (1/min) | t½ (min) | AUClast (min * ng/mL) | AUCinf (min * ng/mL) | MRT (min) |
|---|---|---|---|---|---|---|---|
| N | 13 | 13 | n.d.* | 13 | 13 | 13 | 13 |
| Mean | 9.78 | 20.4 | | 42.1 | 597 | 612 | 67.4 |
| SD | 3.99 | 11.6 | | 10.7 | 107 | 104 | 21.0 |
| Min | 3.92 | 5.0 | | 32.3 | 469 | 474 | 41.1 |
| Median | 8.35 | 20.0 | | 40.3 | 570 | 581 | 61.7 |
| Max | 20.0 | 50.0 | | 67.7 | 886 | 891 | 123 |
| CV % | 40.8 | 57.1 | | 25.4 | 18.0 | 17.0 | 31.1 |
| Geo Mean | 9.11 | 17.5 | | 41.0 | 589 | 604 | 64.8 |

TABLE 10

| Subject | Cmax (ng/mL) | Tmax (min) | λz (1/min) | t½ (min) | AUClast (min * ng/mL) | AUCinf (min * ng/mL) | MRT (min) |
|---|---|---|---|---|---|---|---|
| N | 12 | 12 | n.d.* | 12 | 12 | 12 | 12 |
| Mean | 16.2 | 26.7 | | 40.1 | 996 | 1022 | 541 |
| SD | 3.78 | 9.8 | | 9.83 | 210 | 233 | 155 |
| Min | 9.27 | 10.0 | | 24.9 | 619 | 629 | 238 |
| Median | 17.7 | 25.0 | | 40.1 | 1051 | 1074 | 593 |
| Max | 20.0 | 40.0 | | 62.0 | 1271 | 1410 | 716 |
| CV % | 23.4 | 36.9 | | 24.5 | 21.1 | 22.8 | 28.6 |
| Geo mean | 15.7 | 24.8 | | 39.0 | 973 | 995 | 517 |

In Tables 6-10: * n.d.=not determined. ** V/F is the volume of distribution of the entire dose, and CL/F is the clearance of the entire dose, and these can be normalized and compared between cohorts by multiplying by the relative bioavailability (F): F(injection all doses)=100%, F(Film B)=26%, F(Film F)=18.2%, F(Film E)=16.8% as per Table 9.

Table 11 shows proportionality of Cmax to the dose of apomorphine in each study of the test formulations, even though 4 sets of subjects were tested (not a crossover).

TABLE 11

| Study | Dose (mg) | NCmax (ng/mL/mg) | NAUClast (min * ng/ mL/mg) | NAUCinf (min * ng/ mL/mg) | rBA % |
|---|---|---|---|---|---|
| Film A | 3 | 0.53 | 31.5 | 32.5 | 17% |
| Film B | 8 | 0.51 | 53.1 | 56.5 | 26% |
| Film F | 10 | 0.54 | 50.9 | 54.3 | 18.2% |
| Film E | 15 | 0.54 | 53.6 | 56.9 | 16.8% |

Apomorphine-spiked fresh blood samples also show similar recovery (60%). This observation in combination with the observation of the proportionality in the studies of Films B, E, and F supports the proposition that the present protocol and analytical methods are robust and repeatable/reproducible.

Film D

A single dose study was conducted in healthy male volunteers to assess pharmacokinetics, safety, and tolerability of Film D (apomorphine dose of 25 mg). Anti-nausea medication, domperidone, was administered as part of the study beginning three days prior to and throughout dosing of Film D.

Table 12 provides the comparison of the PK profiles for Films D-F (the data for Films E and F were from the study described above). The Cmax and AUC values indicate that apomorphine exposure was slightly lower than dose proportional, as the dose was raised from 15 to 25 mg. The shortfall in exposure was not large and fell within one standard deviation of the mean values. The data for Film E may have been the outlier on the curve based on its supraproportional exposure.

TABLE 12

| Study | Dose | Normalized $C_{max}$ (ng/ml/mg) | Normalized $AUC_{last}$ (min * ng/ ml/mg) | Normalized $AUC_{inf}$ (min * ng/ ml/mg) | Relative Bioavailability (%) |
|---|---|---|---|---|---|
| Film F | 10 | 0.54 | 50.9 | 54.3 | 18.2 |
| Film E | 15 | 0.54 | 53.6 | 56.9 | 16.8 |
| Film D | 25 | 0.45 ± 0.14 | 44.1 ± 8.6 | 48.2 ± 10.3 | — |

Figure 4:
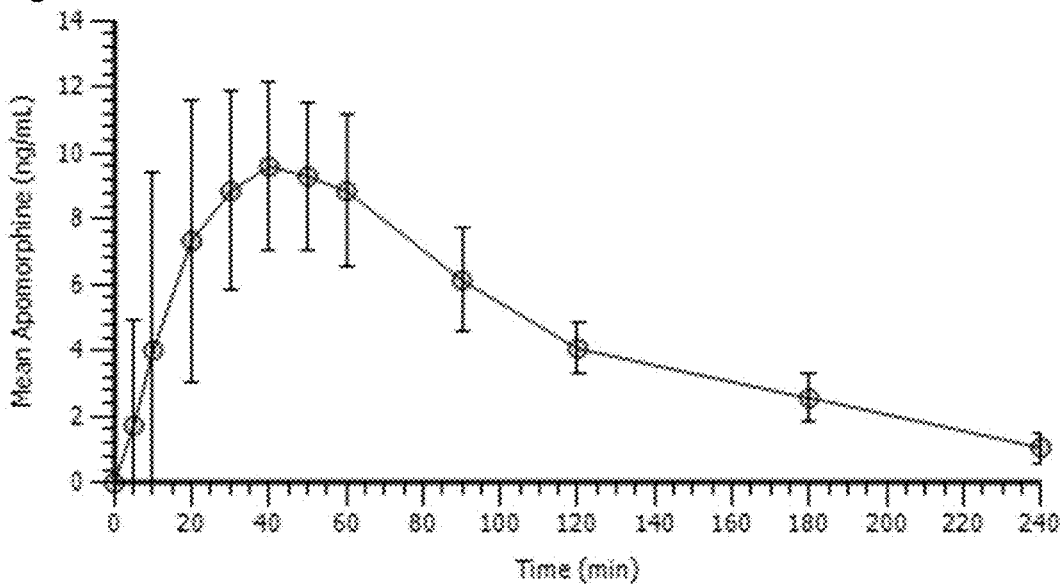
FIG. 4 is a chart showing a pharmacokinetic curve for Film D.

FIG. 4 shows the mean plasma data for Film D. The curve shows that it took ca 8.3 minutes to achieve the hypothesized MEC (3 ng/ml) in subjects. A concentration exceeding the hypothesized MEC was maintained until 153.8 minutes after administration.

Films G, H, I, J, and K

Films G, H, I, J, and K were used in an open-label, single-arm study in 19 patients diagnosed with idiopathic Parkinson's disease consistent with UK Brain Bank criteria. Prior to the start of the study, all patients were experiencing at least one "off" episode per day and a total daily "off" time of 2 hours. The patients were also experiencing predictable "off" episodes in the morning on awakening prior to receiving morning dose of levodopa. All patients were stage Ito II on Hoehn and Yahr scale, when in the "on" state. Table 13 provides a summary of the patients in the study.

TABLE 13

| | |
|---|---|
| Mean Age | 61.5 (48-79) |
| Male:Female | 14 (73.7%):5 (26.3%) |
| Modified Hoehn and Yahr | 2.2 (1-3) |
| Mean # of Daily Off Episodes | 3.9 (1-7) |
| Mean # of PD Medications | 3 (1-5) |
| Mean Daily Levodopa Dose (mg) | 837 (100-1500) |
| Mean # of Levodopa Doses Per Day | 5.3 (1-12) |

Figure 5A:
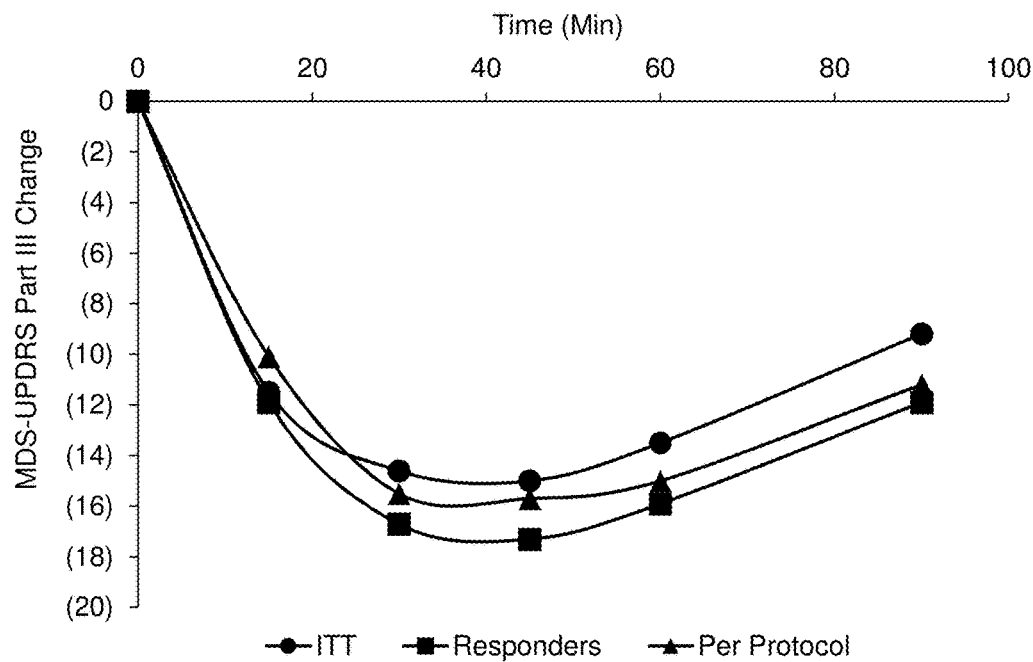
FIG. 5A is a chart showing a reduction in UPDRS Part III (motor function) score of subjects over time following administration of a pharmaceutical unit dosage form of the invention. "ITT" stands for intention to treat and shows the data for all 19 subjects, including those treated per protocol and those incorrectly dosed. "Responders" curve shows the data for 15 subjects that responded to the therapy, including 2 subjects that were not dosed per protocol. "Per protocol" curve shows the data for 15 patients that have received a pharmaceutical unit dosage form of the invention per protocol including two non-responders.
Figure 5B:
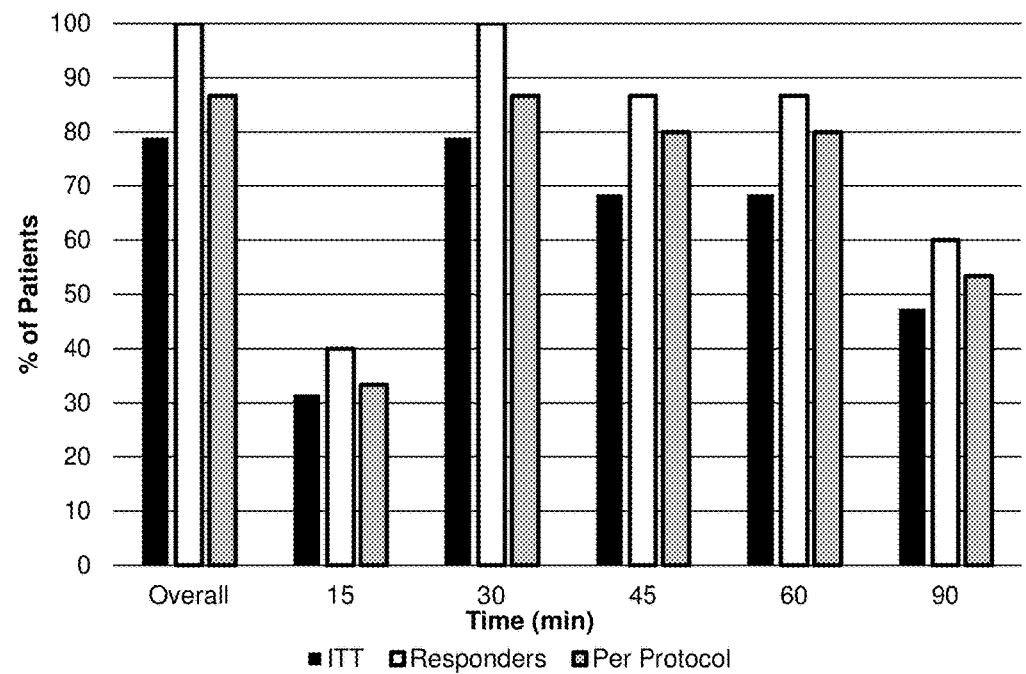
FIG. 5B is a chart showing percentage of subjects that are "on" at each time point after administration of a pharmaceutical unit dosage form of the invention. Each bar corresponds to a patient group, as described in FIG. 5A.
Figure 6A:
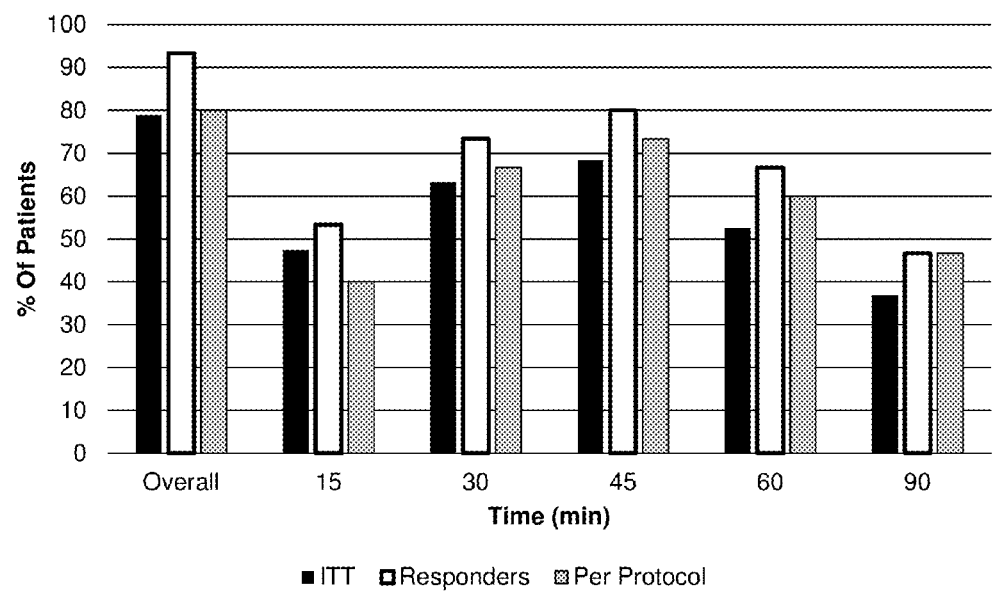
FIG. 6A is a chart showing percentage of subjects that have achieved at least a 30% reduction in UPDRS Part III. Each bar corresponds to a patient group, as described in FIG. 5A.
Figure 6B:
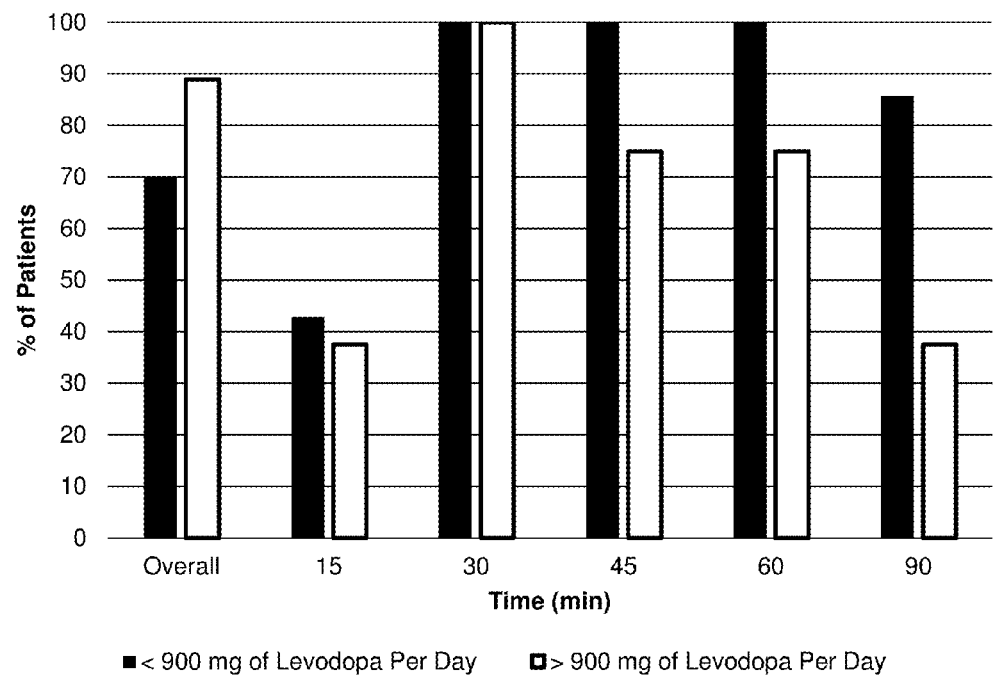
FIG. 6B is a chart showing percentage of subjects achieving a clinically meaningful "on" state. The subjects are divided into two groups: (1) receiving less than 900 mg of levodopa per day and (2) receiving more than 900 mg of levodopa per day.
Figure 7A:
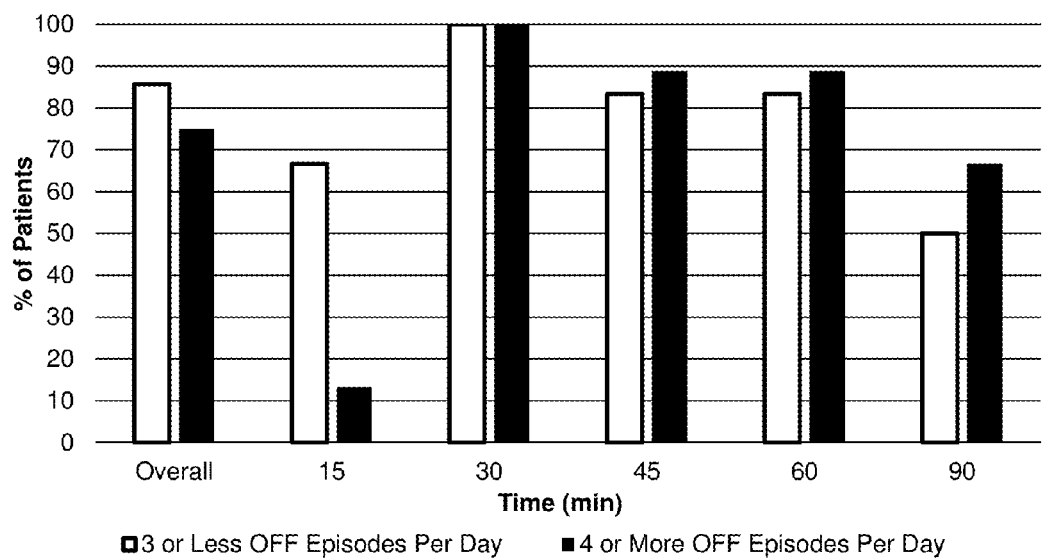
FIG. 7A is a chart showing percentage of subjects achieving a clinically meaningful "on" state. The subjects are divided into two groups: (1) subjects having 3 or fewer "off" episodes per day and (2) subjects having 4 or more "off" episodes per day.
Figure 7B:
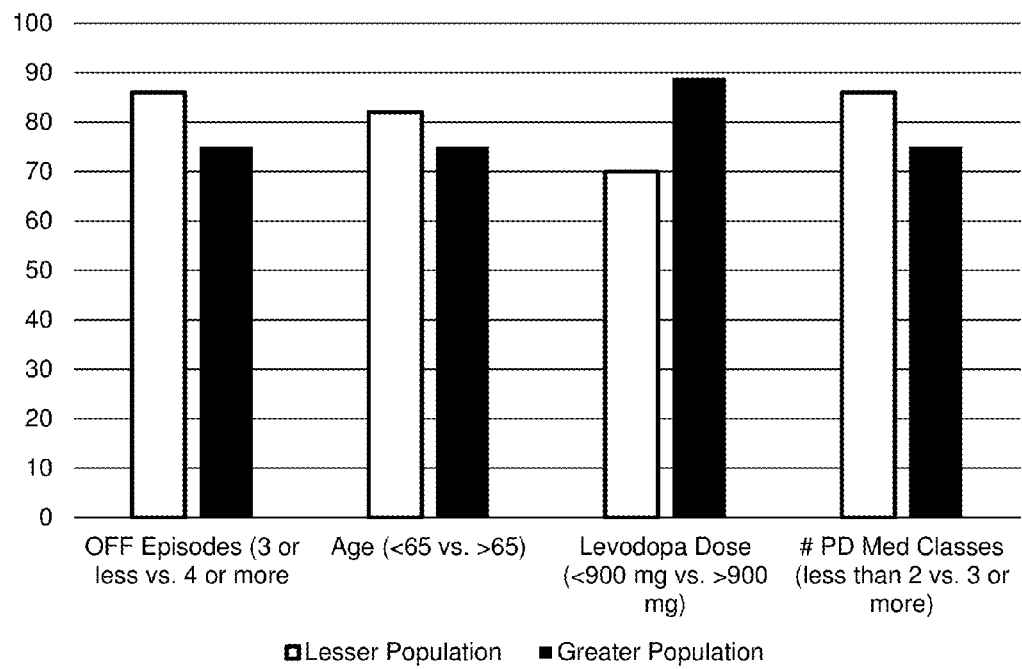
FIG. 7B is a chart showing percentage of subjects achieving a clinically meaningful "on" state among subjects divided into various groups. This figure demonstrates that the pharmaceutical unit dosage forms of the invention may be useful for treating "off" episodes in a broad population of subjects having Parkinson's disease.

Prior to dosing with the films of the invention, the patients were pre-medicated with Tigan® for 3 days. Patients presented to the clinic in the morning in the "off" state (last dose of levodopa was administered no later than 10 PM on the preceding night). Patients were dosed initially with Film K; if a satisfactory response was not observed, the dose was escalated in 5 mg increments (i.e., progression: Film K, Film J, Film I, Film H, and Film G) until a clinically meaningful "on" state was achieved. Patients were dosed up to twice a day on three days. Changes in motor function were evaluated in accordance with UPDRS Part III from pre-dose morning "off" state to post-dose at 15, 30, 45, 60, and 90 minutes (see FIGS. 5A and 5B for results). Of the 19 patients, 15 have achieved a clinically meaningful "on" state within 30 minutes of dosing; 6 have achieved a clinically meaningful "on" state within 15 minutes of dosing (see FIG. 5B). Of the 15 patients achieving "on" state, 13 remained "on" for at least 30 minutes, and 9 remained "on" for at least 60 minutes. As shown in FIG. 6A, majority of responding patients have achieved at least a 30% reduction in UPDRS Part III score within 15 minutes following administration of the film, and overall over 90% of responders have achieved at least a 30% reduction in UPDRS Part III score following administration of the film. As shown in FIG. 6B, among responders, all subjects receiving a high (>900 mg/day) daily dose of levodopa and all subjects receiving a low (<900 mg/day) daily dose of levodopa have been able to achieve a clinically meaningful "on" state after receiving the pharmaceutical unit dosage form of the invention. As shown in FIG. 7A, among responders, all mild, moderate, and severe fluctuators have achieved a clinically meaningful "on" state within 30 minutes following administration of the pharmaceutical unit dosage form of the invention. In summary, FIG. 7B shows that a broad patient population can achieve a clinically meaningful "on" state by undergoing a therapy with a pharmaceutical unit dosage form of the invention.

Figure 8:
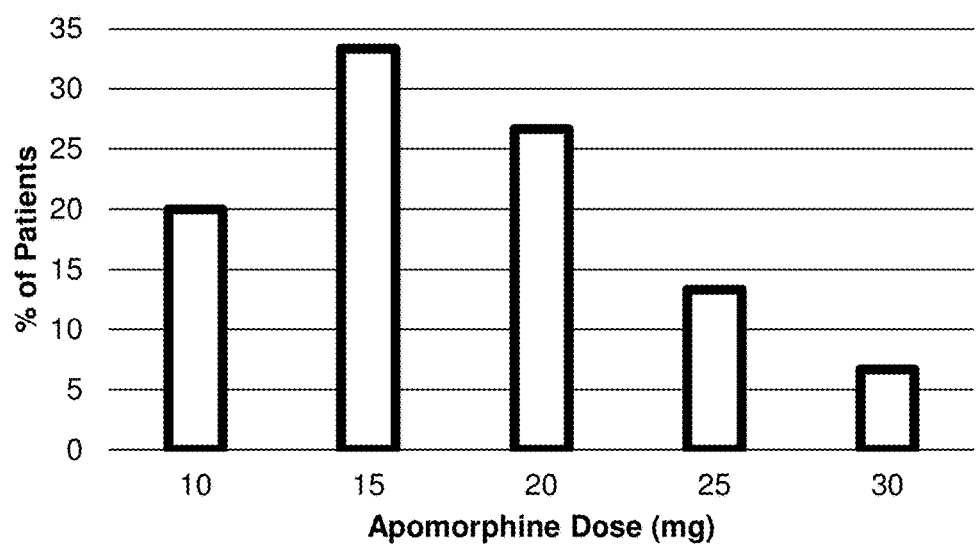
FIG. 8 is a chart showing a percentage of subjects achieving a full "on" state following dosing with the minimal dose of an acid addition salt of apomorphine, as specified in the chart.
Figure 9A:
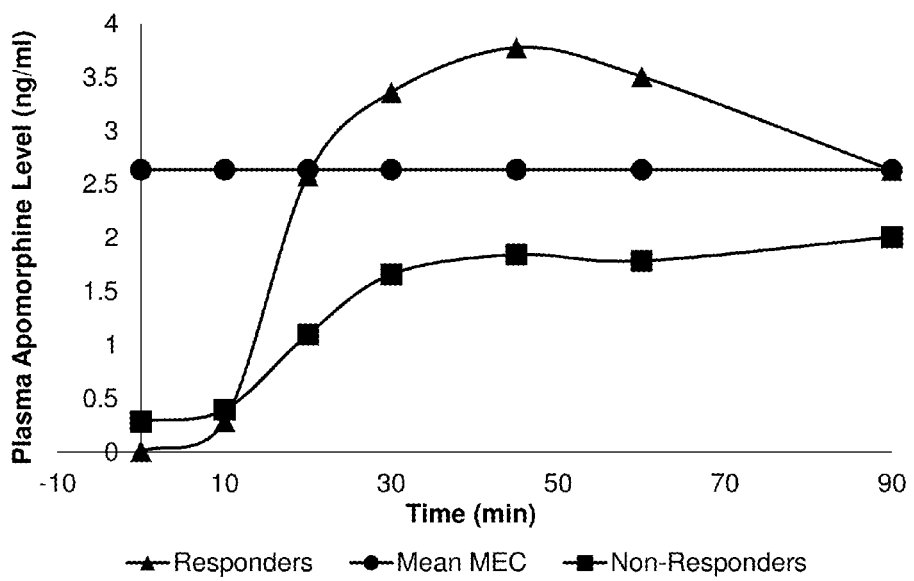
FIG. 9A is a chart showing plasma levels of apomorphine for subjects that have achieved "on" state (responders) and the subjects that have not achieved "on" state (non-responders). The mean minimum effective concentration for apomorphine administered to oral mucosa is shown as "Mean MEC" curve.
Figure 9B:
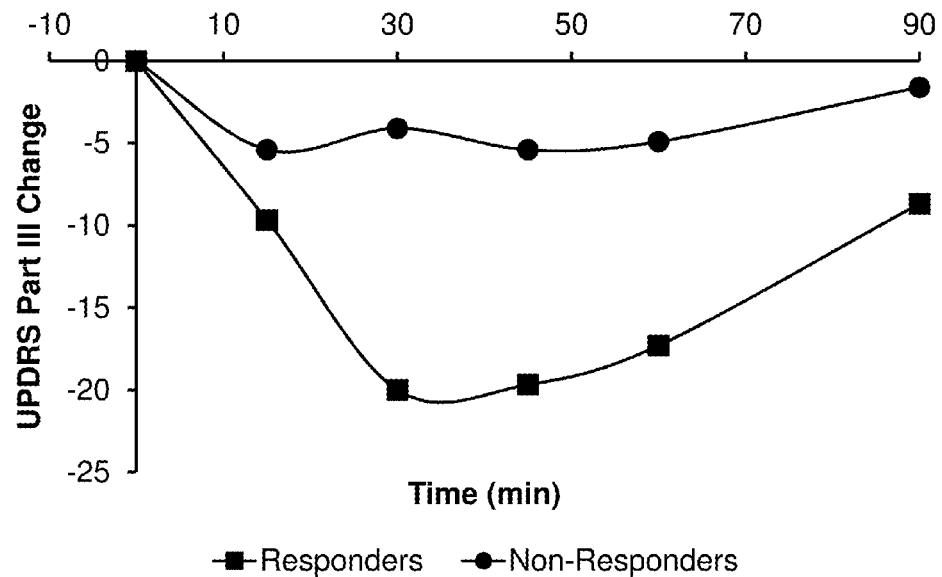
FIG. 9B is a chart showing a reduction in UPDRS Part III (motor function) score of subjects that have achieved "on" state (responders) and the subjects that have not achieved "on" state (non-responders).

A range of doses was used. Over half of the patients needed only the lower two doses (Films J and K), and 80% used Film I, J, or K (FIG. 8; "apomorphine dose" in this Figure indicates the weight of apomorphine hydrochloride in the administered pharmaceutical unit dosage form). Of the 4 patients who did not achieve an "on," 2 were dosed incorrectly, and 2 reached 30 mg without safety or tolerability concerns. Eight patients had pharmacokinetic analyses; six of these eight patients have achieved "on" state. Mean plasma apomorphine concentration upon turning on was 2.64 ng/mL for the six patients. The average plasma apomorphine concentration for the two non-responders for all doses at each time point never reached 2.64 ng/mL. The measured apomorphine plasma levels for responders and for non-responders are shown in FIG. 9A. Responders had large, clinically meaningful UPDRS Part III changes (motor improvement) at all time-points while the non-responders had little motor improvement but not enough to convert from OFF to ON (FIG. 9B).

Example 6

Pharmacodynamics

Pharmacodynamic effects of Film F were estimated from the data in Example 5 and are provided in Table 14.

TABLE 14

| | N reaching >3 ng/ml | Time to 3 ng/ml, min (range) | Duration at >3 ng/ml, min (range) | MRT (min) |
|---|---|---|---|---|
| Film F | 10/13 | 10.6 ± 6 | 56 (30-80) | 101 |
| Film E | 12/12 | 13.6 ± 3 | 106 (55-158) | 102 |
| 2 mg ApoGo | 13/13 | 5.4 ± 3 | 50 (45-55) | 67 |
| 3 mg ApoGo | 12/12 | 3.8 ± 6 | 97 (60-140) | 67 |

From this analysis, the following conclusions can be made. The tested sublingual formulations have a delayed onset to achieve plasma concentration associated with ON, as is evident in the PK profile. The delay can be estimated to be approximately 5-10 min relative to ApoGo using the 3 ng/ml plasma concentration of apomorphine as a basis for efficacy. The duration of plasma concentration exceeding 3 ng/ml level shows Film F to be longer-acting than that of ApoGo by about 5 min at each dose comparison. The number of subjects reaching the MTC (minimal toxic concentration), as defined by 8.5 ng/ml from the Apokyn® SBA, is lower for Test Formulations (e.g., Film F) versus ApoGo in both crossover experiments. Using the MRT, a more formal PK estimate of drug residence, the increase in mean time the drug spends in the blood is increased by 50%. Both Film E and Film F remain in the hypothetical therapeutic window defined by 3 ng/ml (MEC) and 8.5 ng/ml (MTC) for similar (to perhaps longer) periods of time compared to 2 mg and 3 mg ApoGo, respectively. Therefore, sublingual administration of the compositions of the invention (e.g., Film E or Film F) can provide the efficacy that is comparable to or exceeding that of subcutaneous administration of ApoGo, but with fewer adverse events, as the number of subjects reaching the MTC is smaller for the compositions of the invention than that in the ApoGo groups. Fewer and less severe adverse events were observed after administration of the compositions of the invention as compared to subcutaneous administration of ApoGo, as is shown in Table 15. The number and percentage (in parentheses) of the adverse events in each treatment arm are shown below.

TABLE 15

| Adverse Event | Film F N = 13 N(%) | SC Apo 2 mg N = 13 N(%) | Film E N = 14 N(%) | SC Apo 3 mg N = 14 N(%) |
| --- | --- | --- | --- | --- |
| Any AE | 5 (38) | 11 (85) | 13 (93) | 12 (86) |
| Related AE | 5 (38) | 9 (69) | 11 (79) | 12 (86) |
| Moderate AE | 2 (15) | 5 (38) | 4 (29) | 11 (79) |
| Sleepiness | 0 | 3 (23) | 11 (79) | 10 (71) |
| Nausea | 2 (15) | 4 (31) | 3 (21) | 8 (57) |
| Dizziness | 3 (23 | 4 (31) | 7 (50) | 7 (50) |
| Vomiting | 0 | 0 | 2 (14) | 5 (36) |
| Yawning | 0 | 0 | 0 | 3 (21) |

Thus, the sublingual administration of the compositions of the invention: (1) is non-invasive versus subcutaneous administration of apomorphine, (2) can provide apomorphine plasma levels within the therapeutic window for relatively longer periods of time than subcutaneous administration of ApoGo, (3) can lead to apomorphine plasma levels within the therapeutic window within a relatively short period of time, and (4) can cause fewer adverse events in patients relatively to the subcutaneous administration of ApoGo.

Films G, H, I, J, and K

Figure 10:
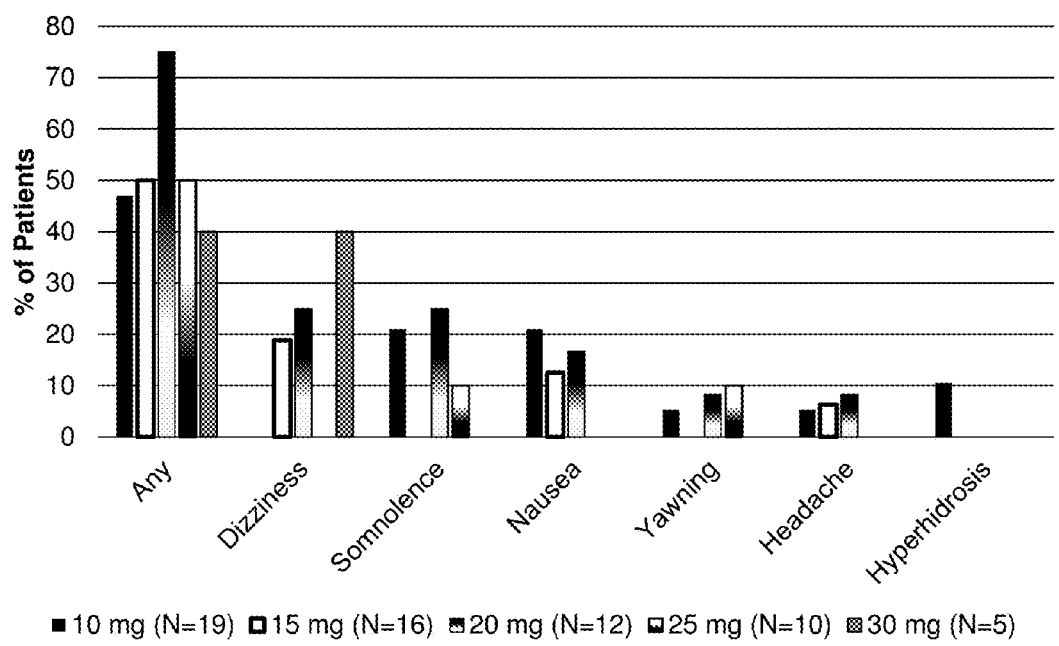
FIG. 10 is a chart showing the percentage of subjects having the listed adverse events relative to the administered dose of apomorphine film.

Summary of adverse events observed during the study described in Example 5 (Films G, H, I, J, and K) is provided in FIG. 10 and Table 16.

TABLE 16

| Preferred Term N = 19 | Any AE N (%) | Mild AE N (%) | Moderate AE N (%) | Severe AE N (%) | Related AE N (%) |
| --- | --- | --- | --- | --- | --- |
| Dizziness | 7 (36.8) | 7 (36.8) | 0 | 0 | 5 (26.3) |
| Somnolence | 6 (31.6) | 3 (15.8) | 3 (15.8) | 1 (5.3) | 5 (26.3) |
| Nausea | 4 (21.1) | 4 (21.1) | 1 (5.3) | 0 | 4 (21.1) |
| Yawning | 3 (15.8) | 3 (15.8) | 0 | 0 | 3 (15.8) |
| Headache | 2 (10.5) | 2 (10.5) | 0 | 0 | 1 (5.3) |
| Hyperhidrosis | 2 (10.5) | 2 (10.5) | 0 | 0 | 2 (10.5) |

In the table above, AE = adverse events.

Example 7

Stability of a Two Layer Apomorphine Strip

Films D-F were individually packaged in sealed foil laminate pouches. The pouches were stored for 1, 2, 3, or 6 months at 5° C., 25° C. (60% RH), 30° C. (65% RH), or 40° C. (75% RH). Impurities detected by HPLC at 0.05 area % are listed by their retention times in Table 17 along with their maximum observed concentration through 6 months of stability testing. Impurity totals are listed in table 18.

TABLE 17

| | Relative Retention Time | | | | | |
| --- | --- | --- | --- | --- | --- | --- |
| | 0.46 | 0.75 | 0.76 | 0.8 | 0.85 | 1.24 | 1.48 |
| Maximum Area % | 0.10 | 0.09 | 0.05 | 0.09 | 0.14 | 0.05 | 0.05 |

TABLE 18

| Film/Storage condition | Month | | | | |
| --- | --- | --- | --- | --- | --- |
| | 0 | 1 | 2 | 3 | 6 |
| Film D/5° C. | 0.05 | 0.13 | — | 0.14 | — |
| Film E/5° C. | 0.08 | 0.13 | — | 0.07 | — |
| Film F/5° C. | 0.14 | 0.15 | — | 0.12 | — |
| Film F/25° C./60% RH | 0.14 | ND | — | 0.06 | .15 |
| Film F/30° C./65% RH | 0.14 | ND | — | 0.06 | 0.2 |
| Film F/40° C./75% RH | 0.14 | ND | 0.08 | 0.05 | 0.14 |

In Table 16, "—" = sample not analyzed at this time point; "RH" = relative humidity; and "ND" = not detected at a level of ≥0.05 Area %.

Color changes were noted in this stability study. Although the color of the dark side of the films appeared stable within human ability to judge color shifts, the lighter blue color on the reverse side of the films was observed to darken somewhat on stability. It is not clear that the color shift is due to a chemical change. In no case did the color of the reverse side become darker than the initial dark blue color on the opposite side of the film, so the color change may be related to dye migrating from one side of the film to the other.

Moisture content appeared to increase slightly from 2.74% at the time of release to 4.6% at the six month time point for the sample held at 40° C./75% RH.

No remarkable changes to the other study parameters (assay, disintegration, bioburden and pH) were observed.

Example 8

Mechanical Properties of Films G-L

Figure 11A:
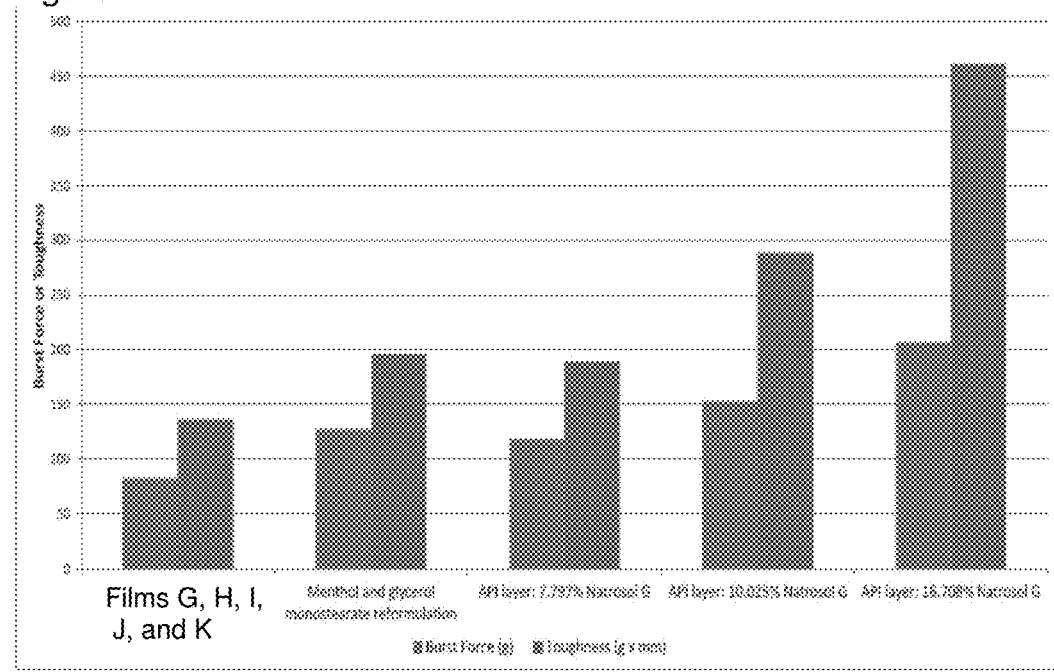
FIG. 11A is a chart showing burst force (g) and toughness (g×mm) for Films G, H, I, J, and K, and films having an apomorphine layer modified as described in the Figure.
Figure 11B:
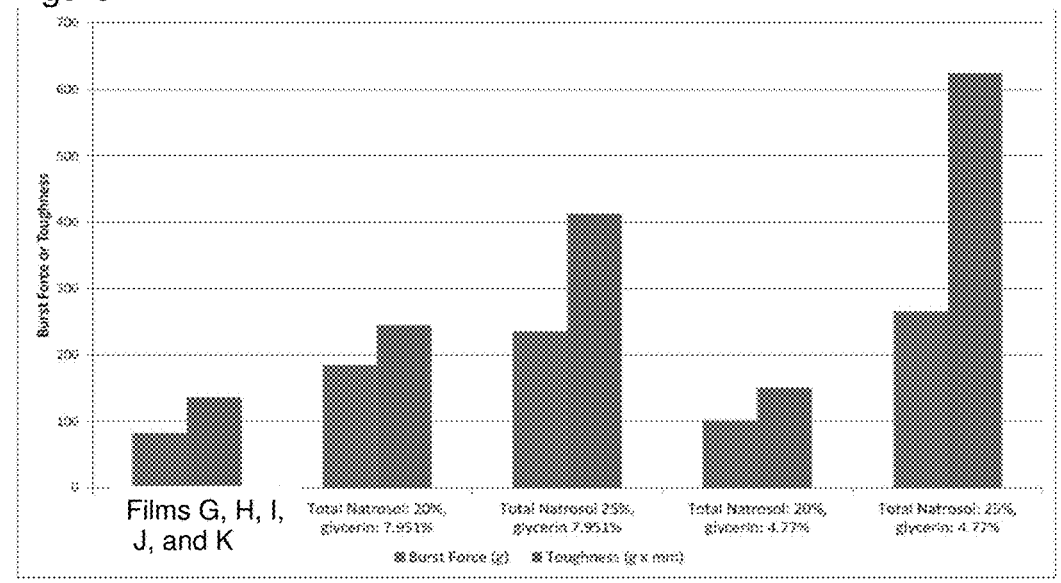
FIG. 11B is a chart showing burst force (g) and toughness (g×mm) for Films G, H, I, J, and K, and films modified as described in the Figure.
Figure 12A:
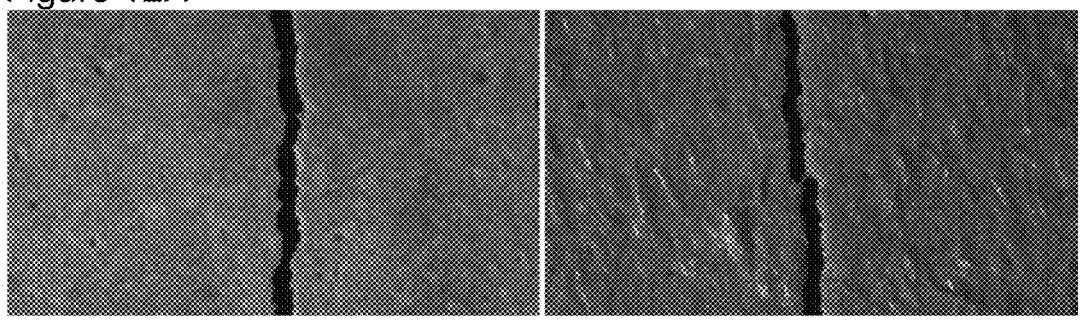
FIG. 12A is a photomicrograph of a pharmaceutical unit dosage form described as Film G, H, I, J, or K after being folded in half.
Figure 12B:
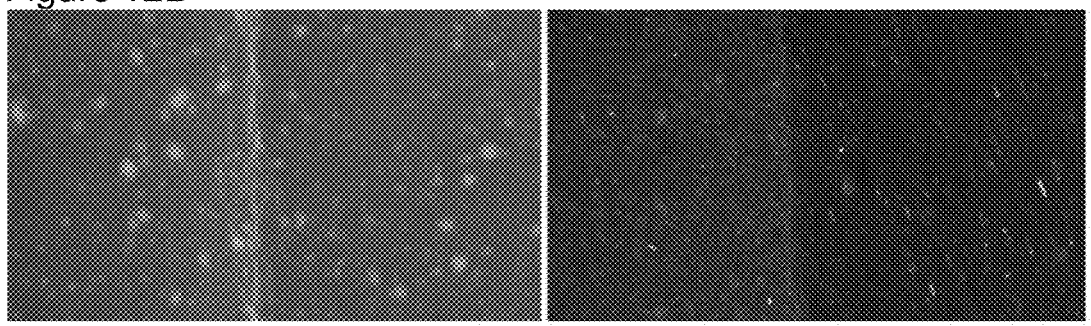
FIG. 12B is a photomicrograph of Film L after being folded in half.

Burst force and toughness were measured for Films G-L. The test was carried out in accordance with *Film and Laminate Puncturing Test*, ASTM F1306. The results of the tests are shown in FIGS. 11A and 11B. Films G-L were subjected to a mechanical test that provides an indication of tear resistance: folding a sample of the film in half. The photomicrographs are shown in FIGS. 12A and 12B.

The disintegration test was carried as out as follows: 15 mL of HPLC grade water were poured in Petri dish. A film was placed on top of the water and allowed to float. The time from placement to disintegration was observed and recorded. Thus, disintegration rate of Films G-K was found to be about 58 second, and the disintegration rate of Film L was found to be about 91 seconds.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A method of treating an "off" episode in a subject having Parkinson's disease, said method comprising:
   (a) providing a film having a first portion comprising apomorphine particles comprising an acid addition salt of apomorphine and a second portion comprising a pH neutralizing agent;

(b) determining an effective dose of said film by up-titration of said subject; and (c) sublingually administering said effective dose of said film to said subject, wherein said effective dose of said film comprises an acid addition salt of apomorphine in an amount sufficient to produce, on average, following administration to the subject: (i) an apomorphine plasma concentration of at least 2.64 ng/mL within 30 minutes, and (ii) an apomorphine Cmax that is less than 10 ng/mL.

2. The method of claim 1, wherein the apomorphine $T_{max}$ is from 20 to 60 minutes following said sublingually administering said film to said subject.

3. The method of claim 1, wherein the film maintains an apomorphine plasma concentration of at least 2.64 ng/mL is maintained for a period of at least 60 minutes.

4. The method of claim 1, wherein said film has a toughness greater than or equal to 100 g × mm.

5. The method of claim 1, wherein said second portion comprises a permeation enhancer.

6. The method of claim 1, wherein said first portion comprises a permeation enhancer.

7. The method of claim 1, wherein said first portion is free of a permeation enhancer.

8. The method of claim 1, wherein said film comprises 20% (w/w) or more of a pharmaceutically acceptable high molecular weight polymer having a weight average molecular weight of 60 kDa or greater.

9. The method of claim 8, wherein said film comprises from 20% (w/w) to 40% (w/w) of said pharmaceutically acceptable high molecular weight polymer.

10. The method of claim 8, wherein said pharmaceutically acceptable high molecular weight polymer has a weight average molecular weight from 60kDa to 1,000 kDa.

11. The method of claim 1, wherein said film comprises 5% (w/w) or less of a pharmaceutically acceptable low molecular weight polymer having a weight average molecular weight of less than 60 kDa.

12. The method of claim 1, wherein said film disintegrates in aqueous media in 2 minutes or less.

13. The method of claim 1, wherein said film comprises 10 ±2.5 mg, 15 ±2.5 mg, 20.0 ±2.5 mg, 25.0 ±2.5 mg, 30.0 ±5.0 mg, or 35.0 ±5.0 mg of said acid addition salt of apomorphine.

* * * * *